(12) United States Patent
Cosgrove

(10) Patent No.: US 6,682,738 B1
(45) Date of Patent: Jan. 27, 2004

(54) β-EXPANSINS AS CELL WALL LOOSENING AGENTS, COMPOSITIONS THEREOF AND METHODS OF USE

(75) Inventor: Daniel J. Cosgrove, Pennsylvania Furnace, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/071,252

(22) Filed: May 1, 1998

Related U.S. Application Data

(60) Provisional application No. 60/045,445, filed on May 2, 1997.

(51) Int. Cl.[7] .............................................. A61K 35/78
(52) U.S. Cl. .................................... 424/185.1; 530/379
(58) Field of Search .......................... 530/379; 514/12; 435/410; 424/185.1

(56) References Cited

PUBLICATIONS

Skolnick et al. TISTECH, vol. 18, pp. 34–39, 2000.*
Brenner et al. PNAS vol. 95 pp 6073–6078 May 1998.*
Cosgrove, D.J. et al. Group I allergens of grass pollen as cell wall–loosening agents. Proc. Natl. Acad. Sci. U.S.A. 94:6559–6564, Jun. 1997*
Roitt, I.M. Encyclopedia of Immunology. Immunoglobulin Fold, E.A. Padlan, pp827–828. Immunoglobulin Gene Superfamily. P.J. Delves & I.M.Roitt. pp831–833. Academic Press, London, 1992.*
Shcherban, T.Y. Molecular cloning and sequence analysis of expansins—a highly conserved, multigene family of proteins that mediate cell wall extension in plants. Proc. Natl. Acad. Sci. U.S.A. 92:9245–9249, Sep. 1995.*
Perez, M. et al. cDNA cloning and immunological characterization of the rye grass allergen Lol P I. J. Biol. Chem. 265:16,210–16,215, Sep. 25, 1990.*
Merriam–Webster's Collegiate Dictionary. pp. 1027 and 1236, Springfield, MA, 1966.*
Sinnott, E.W. Botany: Principles and Problems. 2nd. Edition. McGraw–Hill, New York, 1929.*
Cosgrove, D.J. Characterization of long–term extension of isolated cell walls from growing cucumber hypocotyls. Planta 177:121–130, Feb. 28, 1989.*
Crowell, D.N. Cytokinin regulation of a soybean pollen allergen gene. Plant Mol. Biol. 25:829–835, Aug. 1994.*
McQueen–Mason, "Two Endogenous Proteins That Induce Cell Wall Extension in Plants," The Plant Cell, American Society of Plant Physiologists, p. 1425–1433, (May 24, 1992).
Broadwater, "Zea ml, The Maize Homolog of the Allergen–Encoding Lol pl Gene of Rye Grass," Gene, Slsevier Science Publishers, p. 227–230, (May 24, 1993).
Perez, "cDNA Cloning and Immunological Characterization of the Rye Grass Allergen Lol pl," The J. of Biological Chemistry, the American Society for Biochemistry and Molecular Biology, Inc., vol. 265 (No. 27), p. 16210–15, (May 24, 1990).

Griffith, "Cloning and Sequencing of Lol pl, The Major Allergenic Protein of Rye–Grass Pollen," Federation of European Biochemical Societies, Elsevier Science Publishers, vol. 279 (No. 2), p. 210–21, (May 24, 1991).
Staff, "Cellular Localization of Water Soluble, Allergenic Proteins in Rye–Grass (Lolium Perenne) Pollen Using Monoclonal and Specific IgE Antibodies with Immunogold Probes." Histochemical Journal, Chapman and Hall Ltd., p. 276–290, (May 24, 1990).
Esch, "Identification and Localization of Allergenic Determinants On Grass Group I Antigens Using Monoclonal Antibodies," The J. of Immunology, The American Association of Immunologists, vol. 142 (No. 1), p. 179–184, (May 24, 1989).
McQueen–Mason, "Expansin Mode of Action On Cell Walls," Plant Physiology, p. 87–100, (May 24, 1995).
Knox, "Pollen Allergens: Development and Function," Sex Plant Reproduction, Springer–Verlag, p. 318–323, (May 24, 1996).
Knox, "Environmental and Molecular Biology of Pollen Allergens," Trends in Plant Science, Elsevier Science Ltd., vol. 1 (No. 5), p. 156–164, (May 24, 1996).
Heslop–Harrison, "The Pollen–Stigma Interaction In the Grasses," Acta Botany Neerl., vol. 33 (No. 1), p. 81–99, (May 24, 1984).
Smith, "Molecular Characterization of Group I Allergens of Grass Pollen," Pollen Biotechnology, p. 125–143.
Heslop–Harrison, "The Pollen–Stigma Interaction In the Grasses," Acta Bot. Neel., p. 193–211, (May 24, 1985).
Wu, "Growth Maintenance Of the Maize Primary Root At Low Water Potentials Involves Increase In Cell–Wall Extension Properties, Expansin Activity, and Wall Susceptibility to Expansins," Plant Physiology, p. 765–772, (May 24, 1996).
Cosgrove, "Role of Expansin In Cell Enlargement of Oat Coleoptiles," Plant Physiology, p. 1321–1328, (May 24, 1993).
Shcherban, "Molecular Cloning and Sequence Analysis of Expansins—A Highly Conserved, Multigene Family of Proteins That Mediate Cell Wall Extension In Plants," Plant Biology, Proc. Natl. Acad. Sci., p. 9245–9249, (May 24, 1995).

* cited by examiner

*Primary Examiner*—Patrick J. Nolan
(74) *Attorney, Agent, or Firm*—McKee, Voorhees & Sease, P.L.C.

(57) ABSTRACT

The present invention relates to proteins belonging to a novel class of proteins designated as β-expansins, a composition comprising such proteins, isolated polynucleotides encoding β-expansins, methods for using the polynucleotides and proteins of the invention and methods for identifying, isolating and purifying expansins, including α and β-expansins. Beta-expansins of the invention have the property of altering physical properties of a plant cell wall, such as for example by loosening or expanding plant cell walls.

11 Claims, 9 Drawing Sheets

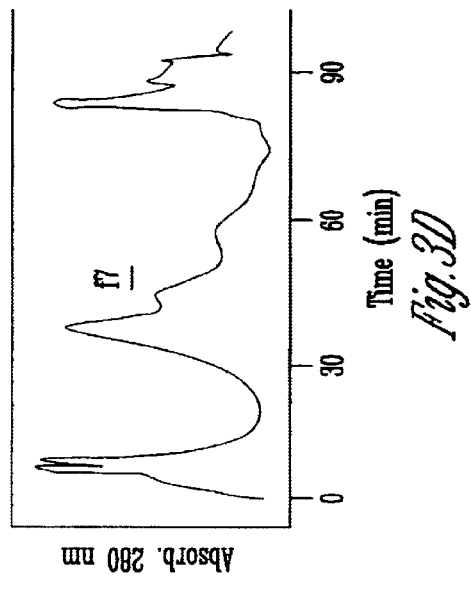
Fig. 3D
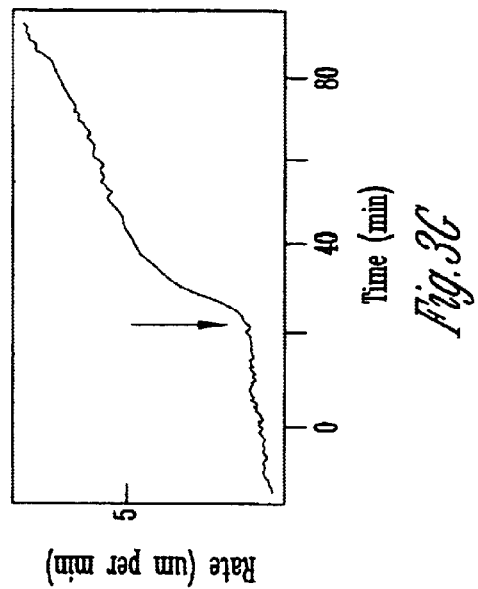
Fig. 3C
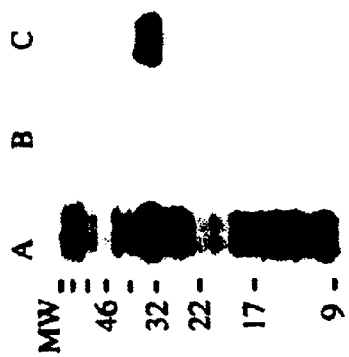
Fig. 3A,B,C
Fig. 3E,F

β-EXPANSINS AS CELL WALL LOOSENING AGENTS, COMPOSITIONS THEREOF AND METHODS OF USE

This application claims priority under 35 U.S.C. §119 of a provisional application Ser. No. 60/045,445 filed May 2, 1997, which provisional application is hereby incorporated by reference in its entirety.

This research was supported by the grants MCB-9317864 from the US National Science Foundation. The United States Government may have some rights in this invention.

FIELD OF THE INVENTION

The present invention relates to proteins belonging to a novel class of proteins designated as β-expansins, a composition comprising such proteins, isolated polynucleotides encoding β-expansins, methods for using the polynucleotides and proteins of the invention and methods for identifying, isolating and purifying expansins, including α and β-expansins.

BACKGROUND OF THE INVENTION

Many grasses, such as rye grass, Kentucky bluegrass and orchard grass, release prodigious quantities of wind-dispersed pollen that trigger hayfever, seasonal asthma and related immune reactions in humans. Up to 25% of adults suffer these allergic responses as a result of inhaling pollen-laden air. (Knox, B. et al., (1996) *Trends in Plant Science* 1:156–164.) The major and most wide-spread allergenic component of grass pollen are the group I allergens. (Griffith, I., et al, (1991) *FEBS Lett.* 279:210–215; Perez, M., et al., (1990) *J. Biol. Chem.* 265:16210–16215; Esch, R. E. et al., (1989) *Mol. Immunol.* 26:557–561.) These are glycoproteins of about 30 kD that are quickly and profusely released by grass pollen upon hydration; in humans they bind to IgE antibodies to initiate the allergic response. Pollen from grasses contain one or more forms of these allergens, which are named after the source species, e.g. Lol pI is from *Lolium perenne* (rye grass), Ory sI is from *Oryza sativa* (rice), etc. Although the immunological aspects of these allergens, especially Lol pI, have been extensively studied, their biological function in the plant is unknown. Nevertheless, high sequence conservation among homologs in divergent grass species implies that they serve a vital biological function. (Xu, H. L., et al., (1995) *Gene* 164:255–259; Broadwater, A. H., et al., (1993) *Gene* 131:227–230.)

Recently, Shcherban et al. (Shcherban, T. Y., et al., (1995) *Proc. Natl. Acad. Sci. USA*, 92:9245–9249) noted that group I pollen allergens have a distant sequence similarity to expansins. Expansins are extracellular proteins that promote plant cell wall enlargement, evidently by disrupting noncovalent bonding between cellulose microfibrils and matrix polymers. (McQueen-Mason, S., et al. (1994) *Proc. Natl Acad. Sci. USA* 91:6574–6578; McQueen-Mason, S. et al., (1992) *Plant Cell* 4:1425–1433.) These previously described expansins are referred to in this specification as alpha-expansins. Applicant has now surprisingly discovered that the group I pollen allergens are structurally and functionally related to expansins and that they comprise a second family of expansins, β-expansins.

SUMMARY OF THE INVENTION

The present invention relates to β-expansins, including vegetative homologs of β-expansins, compositions thereof and isolated polynucleotides encoding the β-expansins of the invention. Beta-expansins, and polynucleotides encoding -expansins, of the invention may be of natural origin, isolated and purified or recombinatly produced. For purposes of the present invention, a "vegetative homolog" is defined as a β-expansin which is originally found in any plant part but pollen.

In one aspect, the invention relates to a polypeptide belonging to a class of β-expansins such as, for example, a group I grass pollen allergen and a vegetative β-expansin and compositions thereof.

In another aspect, the invention relates to a polynucleotide encoding the β-expansin of the invention, and a vector, a host cell and a transgenic plant comprising said polynucleotide.

In yet another aspect, the invention relates to a method of altering physical properties of the plant cell wall or any cell wall products derived from plant material, for example paper or textile.

In a further aspect, the invention relates to a method of identifying, isolating and purifying an expansin protein (including both α and β-expansins) or a polynucleotide encoding such protein.

DESCRIPTION OF THE DRAWINGS

FIG. 3 shows dentification of Zea ml in maize pollen extracts and its association with wall extension activity. (A) Coomassie-stained SDS polyacrylamide gel of total proteins eluted from maize pollen. (B) Western blot of total proteins eluted from maize pollen, using rabbit polyclonal antibodies against cucumber ("S1", Cs-EXP1 expansin (Shcherban 1995; Li, Z.-C., et al. (1993) *Planta* 191:349–356, 14). (C) Western blot of total proteins eluted from maize pollen, using monoclonal antibody directed against a Lol pI fragment (site D). (Esch 1989). (D) Fractionation of maize pollen protein on CM-Sepharose. (E) Coomassie-stained SDS-PAGE and (F) western blot of CM-Sephadex fraction (f7) with highly purified Zea ml protein. (G) Extension curve of heat-inactivated walls of maize silks treated (arrow) with purified Zea ml (fraction f7) brought to pH 4.5 with sodium acetate buffer.

FIG. 5 shows an amino acid alignment of seven β-expansins prepared using the Clustal algorithm. Strictly conserved residues are boxed in. The following sequences are represented: z37641 SEQ ID NO:18.PRO (Genbank U95967 SEQ ID NO:1); zeam1a.PRO (Genbank L14271 SEQ ID NO:18); Lolp1.PRO (Genbank M57474 SEQ ID NO:18); OsEXP1beta.PRO (Genbank U95968 SEQ ID NO:18); cim1.PRO (Genbank U03860 SEQ ID NO:20) beta2 predicted protein (unpublished) SEQ ID No. 17; and z37641.PRO (Genbank U95967 SEQ ID NO:21).

FIG. 6 shows an amino acid alignment of four β and four α-expansins prepared using the Clustal algorithm. Strictly conserved residues are boxed in. The following sequences are represented: Lolp1.PRO (Genbank M57494); OsEXP1beta.PRO (Genbank U95968); CuEXP1SIGN.PRO (Genbank U30482 SEQ ID NO:22); CuEXP2sign.PRO (Genbank U30460 SEQ ID NO:23); OsEXP1.PRO (Genbank Y07782 SEQ ID NO:36); AtEXP1.PRO (Genbank U30476 SEQ ID NO:37).

DETAILED DESCRIPTION OF THE INVENTION

Figure 1A:
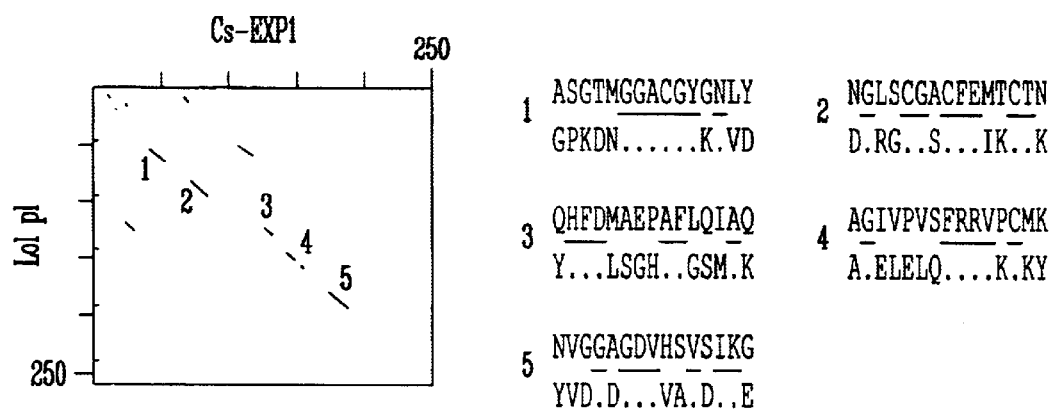
FIG. 1 shows a structural comparisons of alpha-expansins and group I allergens. (A) Dot plot of Cs-EXP1 (Genbank U30382) with Lol pI (Genbank X57678) shows limited, but distributed, sequence similarity. Alignments of the most conserved regions (1 to 5) are shown at right (1-SEQ ID NO.s:24 and 25; 2-SEQ ID NO.s:26 and 27; 3-SEQ ID NO.s:28 and 29; 4-SEQ ID NO.s:30 and 31; 5-SEQ ID NO.s:32 and 33). Conserved amino acids are underlined in the top line and represented by a period (.) in the lower line. (B) Secondary structure predictions for expansins and allergens show close similarity between these two groups of proteins. Regions of the protein with a PHDsec score<7 are shown as open (unpatterned) blocks. Arrows mark two notable disagreements in the predicted structures. The expansin prediction was based on Genbank sequences U30460, U30476, U30477, U30478, U30479, U30480, U30381, U30382, X85187, Y07782, U85246. The allergen prediction was based on Genbank sequences U31771, M57474, U03860, L14271, X78813, Z27084, A31060, Z27090. Signal peptides were removed from the sequences before analysis. (C) Hydrophobic cluster analysis of the allergen Lol pI and expansin Cs-EXP I indicates good concordance between the two proteins. Shaded boxes demarcate putative homologous hydrophobic clusters. Domains of high sequence similarity are outlined with dotted lines and were used as "landmarks" to identify homologous clusters. The conserved regions in A are also indicated in B and C (numbered 1 to 5). The conserved cysteines are found in the dotted regions 1, 2, and 4.

All patents, patent applications and publications cited herein are hereby incorporated by reference. In case of inconsistencies the present disclosure governs.

The present invention relates to proteins belonging to a novel class of proteins designated as β-expansins, a composition comprising such proteins, polynucleotides encoding β-expansins (and vectors, host cells and plants containing such polypeptides), a method for using the polynucleotides and proteins of the invention, and a method for identifying, isolating and purifying expansins, including both α and β-expansins. Beta-expansins of the invention, and polynucleotides encoding β-expansins, may be of natural origin, isolated and purified or recombinatly produced.

A polypeptide of the invention, referred to as a β-expansin, is a polypeptide having a molecular weight from about 24 kD to about 35 kD, preferably from about 24 kD to about 32 kD, and most preferably from about 25 kD to about 28 kD. When the molecular weight of the protein of the invention is measured by SDS-PAGE using the conditions set forth in the Example, the molecular weight of the polypeptide may be from about 25 to about 35 kD. The polypeptides of the invention include but are not limited to class I pollen allergens and vegetative homologs of such allergens. Beta-expansins of the invention have the property of altering physical properties of a plant cell wall. For purposes of the present disclosure, "altering physical characteristics of a plant cell wall" includes loosening or expanding cell walls, altering cell wall mechanical strength, altering the bonding relationship between the components of the cell wall and/or altering the growth of the plant cell wall. This property of β-expansins of the invention may be determined by using assays well known in the art, such as cell-wall extension and stress relaxation assays. Induction of cell wall extension (creep) and an increase in the stress relaxation spectrum of the wall are diagnostic for expansins (both α and β). Expansins show an effect in these assays at, for example, a dosage of 1 part (and above) protein to 1,000 to 10,000 parts cell wall (on a dry weight basis).

Beta-expansins of the invention are similar to α-expansins described in co-pending U.S. applications Ser. Nos. 08/834,327 filed Apr. 15, 1997 now U.S. Pat. No. 5,990,283 and 08/440,517 now U.S. Pat. No. 5,959,082 filed May 12, 1995 in that they both have the property of inducing stress relaxation and extension of plant cell walls. However, β-expansins have low amino acid sequence similarity with α-expansins, which is about 25% as determined by BLAST or FASTA algorithms. Furthermore, β-expansins are more effective on grass cell walls than on dicotyledon plant cell walls. In contrast, α-expansins are more effective on dicotyledon plant cells walls than on grass cell walls. Since it is known that monocot and dicot cell walls differ in their chemical composition, it is likely that β and α-expansins act on different components of the plant cell wall.

Figure 5:
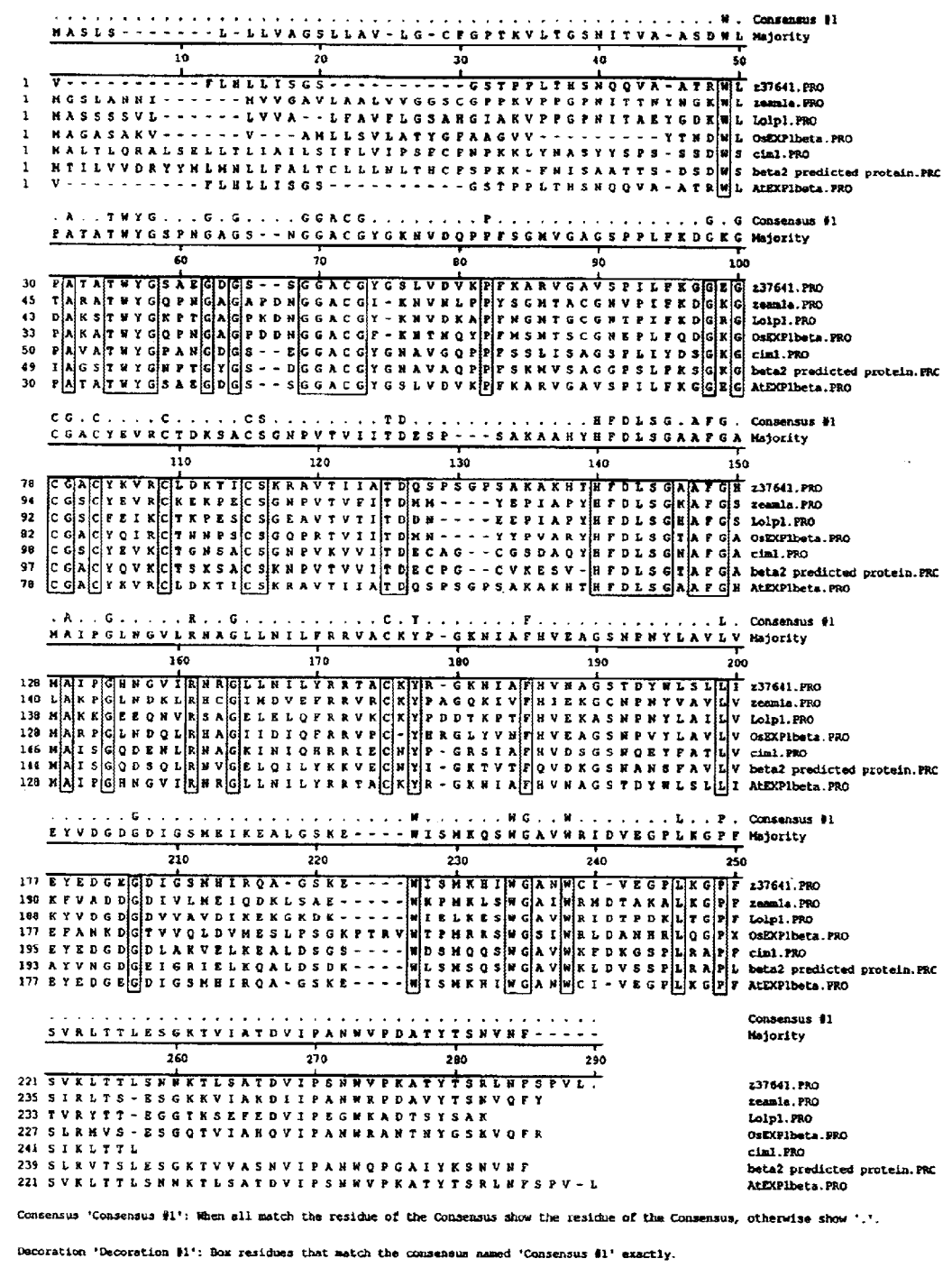

Beta-expansins of the invention are characterized by the following conserved structural elements. With respect to the primary structure, the amino acids and/or amino acid regions outlined as conserved in FIG. 5 are present in β-expansins of the invention as determined by the Clustal alignment algorithm.

Amino acids other than those indicated as conserved will differ among the β-expansins of the invention so that the percent protein similarity between any two β-expansins may vary and may be, for example, 28.5% or up to 60% as determined by using alignment by the Cluster Method and basing similarity on the MEGALIGN algorithm. For purposes of the present invention, any protein that has the conserved regions defined in FIG. 5 and is capable of inducing cell wall extension and stress relaxation as described herein is within the scope of the present invention, even if such a protein is not naturally found and is made according to methods of recombinant technology, provided that such a protein is not an α-expansin.

Figure 1B:
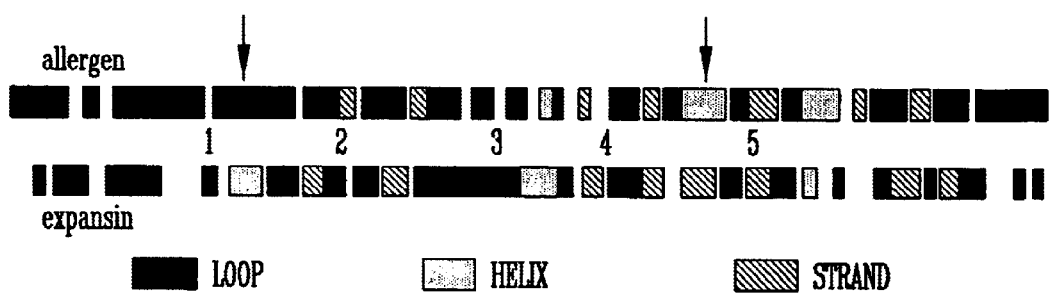

With respect to the secondary structure, β-expansins of the invention may have a secondary structure as shown in FIG. 1B.

β-expansins may be isolated from both monocotyledon and dicotyledon plants. However, β-expansins produced using recombinant DNA technology are also within the scope of the present invention. In one embodiment, β-expansin is of a dicotyledon origin, i.e., it has an amino acid sequence as originally found in a dicotyledon plant, preferably other than soybean.

Figure 4:
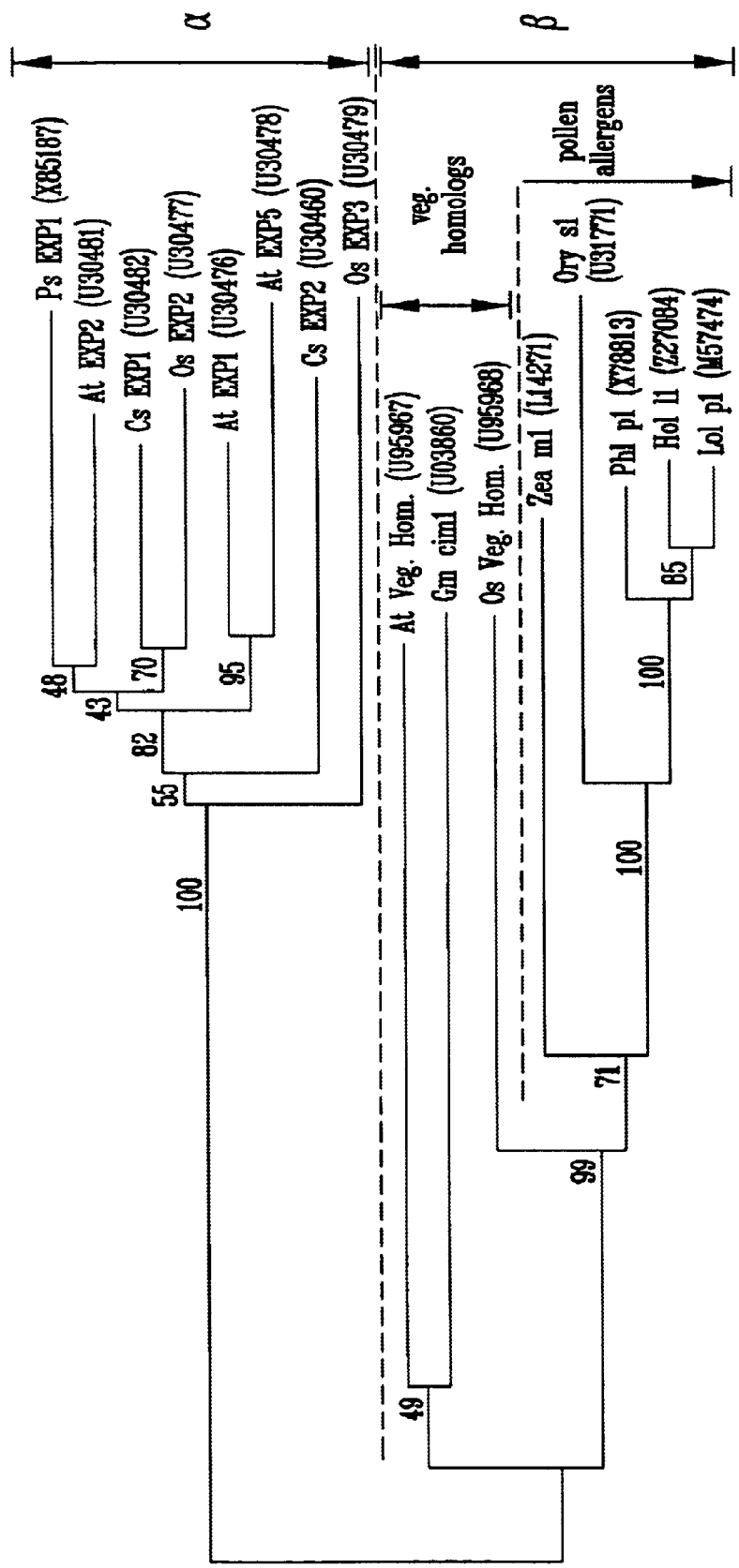
FIG. 4, shows phylogenetic tree of α-expansins, group I allergens, and their vegetative homologs. Protein sequences were aligned using the Clustal program with PAM250 weight table and the tree was constructed by bootstrap analysis (1,000 replications) using nearest neighboring joining of the Poisson-Corrected values for amino-acid differences, using the MEGA phylogenetic analysis program (S. Kumar, K. Tamura aid M. Nei, Institute for Molecular Evolutionary Genetics, Pennsylvania State University). The numbers on the tree indicate the bootstrap P-values. Genbank accession numbers are also indicated for each sequence.

In another embodiment, β-expansins of the invention are class I pollen allergens such as, for example, Zea mI and others listed in FIG. 4.

In one preferred embodiment, β-expansin is a vegetative homolog of a class I grass pollen allergen. More preferably, a vegetative homolog is not of soybean origin, i.e., it does not have an amino acid sequence of the soybean vegetative homolog. Most preferably, the vegetative homolog of the invention is of Arabidopsis or rice origin.

An example of a vegetative homolog of the invention is an Arabidopsis vegetative homolog, which may have the amino acid sequence of SEQ ID NO. 9 (corresponding to nucleotide cDNA sequence deposited with Genbank, U95967). Other vegetative homologs of Arabidopsis having a different amino acid sequence are also within the scope of the present invention.

Another example of a vegetative homolog is a rice vegetative homolog, which may have the amino acid sequence of SEQ ID NOS. 10, 11, 12, 13, 14 and 15. In one embodiment, the rice vegetative homolog is a full length polypeptide, i.e., it is of the same length as originally present in rice tissues.

Function-conservative variants of β-expansins for which amino acid sequences are specifically disclosed herein (e.g. Arabidopsis and rice) are also within the scope of the present invention. A "function-conservative variant" of SEQ ID NO. 9, for example, is a polypeptide which has at least 60% amino acid identity as determined by BLAST or FASTA algorithms, preferably at least 75%, most preferably at least 85%, and even more preferably at least 90%, and which has the property to function as a β-expansin.

In one embodiment, a β-expansin of the invention is a full length polypeptide. For purposes of the present disclosure, a "full length polypeptide" indicates that the β-expansin has the same number of amino acids as the polypeptide originally found in plant tissues. However, continuous fragments of β-expansins are also within the scope of the invention. A "continuous fragment" is a fragment of a β-expansin polypeptide without an internal deletion. Such fragments are at least 20 amino acids long, preferably at least 100 and most preferably at least 200 amino acids long. The fragments of the invention have the property of altering physical properties of a plant cell wall, which can be determined by stress relaxation and wall extension assays. These assays are well known in the art and are described in the Example. The crucial residues in β-expansins are those between positions 55 and 238 in FIG. 5, that is, starting with "TWYG" and ending with the "W" at position 238. The most diagnostic motifs are the conserved GGGACG (SEQ ID NO:34) box at position 69, the conserved cysteines (C) at positions 101, 104, 109, and 176, the HFDL region of the HFDLSG (SEQ ID NO:35) box at position 140, and the tryptophans (W) at positions 227, 234, and 238.

β-expansin polypeptide fragments that do not have the property to function as β-expansins but contain at least one of the conserved regions shown in FIG. 5 (and listed above) are also within the scope of the present invention. Such polypeptide fragments are useful for raising antibodies which can then be used to identify and purify other β-expansins.

"Purification" of a β-expansin polypeptide refers to the isolation of the polypeptide in a form that allows its activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the β-expansin protein or against peptides derived therefrom can be used as purification reagents. Other purification methods are possible.

The present invention also relates to a composition containing a β-expansin polypeptide. The composition has the property of altering the physical characteristics of a plant cell wall or of any material containing such cell walls (e.g. paper, textile). Preferably, the composition contains an acid medium. Preferably, the pH of the acid medium is in the range of 3.0–5.5 and additionally may comprise a sulfhydryl reducing agent. The pH range is more preferably about 3.5–5 and most preferably is about 4.0. Suitable acid buffers include acetate, citrate, and other organic acids.

Buffer concentrations in the composition of the invention are preferably from about 20 to about 100 mM. In other embodiments of the invention at least 1 mM or at most 500 mM is used. Urea, for example at about 1–2 M, may act synergistically with expansins. Calcium chelators, such as EGTA, EDTA, CDTA, at for example about 1–50 mM can aid expansin action. Thiol reductants such as dithiothreitol or bisulfite, for example at about 1–10 mM may also be used. However, the only essential ingredient is the expansin protein (for example at a concentration of about 1–10 micrograms per mL). In one embodiment, at least 0.1 micrograms per mL may be used (higher than 10 micrograms per mL is very effective, but may be wasteful of the protein).

The present invention also relates to polynucleotides encoding the polypeptides of the invention. A "polynucleotide" is intended to include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

Polynucleotides encoding β-expansins of the invention may be isolated from both monocotyledon and dicotyledon plants. Other plant sources, such as gymnosperms, ferns and mosses, are also within the scope of the present invention. However, β-expansin-encoding polynucleotides produced by using recombinant DNA technology are also within the scope of the present invention. In one embodiment, a polynucleotide encodes a β-expansin of a dicotyledon origin, i.e., it has a nucleotide sequence identical to the one originally found in a dicotyledon plant, preferably other than soybean.

In another embodiment, polynucleotides of the invention encode class I pollen allergens such as, for example, Zea MI and others listed in FIG. 4.

In one preferred embodiment, a polynucleotide of the invention encodes a vegetative homolog of a class I grass pollen allergen. In one embodiment, a polynucleotide encodes a vegetative homolog not of soybean origin, i.e., it does not have a nucleotide sequence of the soybean vegetative homolog DNA, cDNA or RNA. Preferably, polynucleotides of the invention encode vegetative homologs of Arabidopsis or rice origin.

An example of a polynucleotide encoding an Arabidopsis vegetative homolog is presented herein as SEQ ID NO. 1 (deposited with Genbank, U95967). Polynucleotides encoding other vegetative homologs of Arabidopsis and having a nucleotide sequence different from SEQ ID NO. 1 are also within the scope of the present invention.

Another example of a polynucleotide encoding a vegetative homolog, is a polynucleotide encoding a rice vegetative homolog, which may encode the amino acid sequence of SEQ ID NOS. 2 (Genbank, U85968), 3, 4, 5, 6, and 7. In one embodiment, the polynucleotide encodes a full-length rice vegetative homolog, i.e., of the same length as originally present in rice tissues.

Sequence-conservative and function-conservative variants of polynucleotides encoding β-expansins are also within the scope of the present invention. "Sequence conservative variants" are those in which a change of one or more nucleotides in a given codon position results in no alteration in the amino acid encoded at that position. "Function-conservative variants" are those in which a given amino acid residue in a encoding β-expansin has been changed without altering the overall conformation and function of the polypeptide, including, but not limited to, replacement of an amino acid with one having similar physico-chemical properties (such as, for example, acidic, basic, hydrophobic, and the like). Amino acids which have similar physico-chemical properties are well known in the art. For example, arginine, histidine and lysine are hydrophilic-basic amino acids and may be interchangeable. Similarly, isoleucine, a conservative variants of β-expansins may encode at least some of the conserved amino acids/ regions represented in the alignment in FIG. 5. The crucial amino acid residues are pointed out above.

In one embodiment, β-expansin polynucleotide of the invention is a full length polynucleotide. For purposes of the present disclosure, a "full length polypeptide" indicates that the β-expansin has the same number of nucleotides as the polynucleotide originally found in plant tissues. However, continuous fragments of β-expansin polynucleotides are also within the scope of the invention. A "continuous fragment" is a fragment of a β-expansin polynucleotide without an internal deletion. Such fragments are at least 60 nucleotides long, preferably at least 300 nucleotides and most preferably at least 600 nucleotides long. The polynucleotide fragments encode polypeptides that have the property of altering physical properties of a plant cell wall, which can be determined by stress relaxation and wall extension assays.

The polynucleotides of the invention may be isolated directly from cells using appropriate labelled probes containing, for example, regions of high conservation among β-expansins. Alternatively, PCR can be used to produce the polynucleotides of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The polynucleotides of the present invention may be flanked by natural regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotide sequences of the present invention may also be modified with a label capable of providing a detectable signal, either directly or indirectly. Exemplary labels include radioisotopes, fluorescent molecules, biotin, and the like.

The invention also provides nucleic acid vectors comprising the polynucleotides is of the invention or derivatives or fragments thereof. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP (Invitrogen, San Diego, Calif.), T-DNA in Agrobacterium, and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Suitable host cells may be transformed/transfected/infected as appropriate by any suitable method including electroporation, $CaCl_2$ mediated DNA uptake, fungal infection, microinjection, microprojectile-mediated transformation, Agrobacterium-mediated transformation, or other established methods.

Appropriate host cells include bacteria, archaebacteria, fungi, especially yeast, and plant and animal cells. Of particular interest are E. coli, B. subtilis, Saccharomyces cerevisiae, Saccharomyces carlsbergensis, Schizosaccharomyces pombi, SF9 cells, C129 cells, 293 cells, Drosophila cell lines, Neurospora, Pichia, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced β-expansins or derived peptides and polypeptides. For plant transformation, DNA may be cloned into casettes based on T-DNA plasmids, propagated in *E. coli* or Agrobacterium, and used to stably transform plants by the Agrobacterium method. Alternatively, DNA may be inserted into suitably modified plant viruses, such as tobacco mosaic virus, and used to produce recombinant protein by infection of tobacco plants or other sensitive plant species.

Vectors may also include a transcription regulatory element (a promoter) operably linked to the β-expansin sequence. The promoter may optionally contain operator portions and/or ribosome binding sites. Non-limiting examples of bacterial promoters compatible with *E. coli* include: trc promoter, alpha-lactamase (penicillinase) promoter; lactose promoter; tryptophan (trp) promoter; arabinose BAD operon promoter; lambda-derived P1 promoter and N gene ribosome binding site; and the hybrid tac promoter derived from sequences of the trp and lac UV5 promoters. Non-limiting examples of plant promoters include: CaMV 35S, PR1, PR, auxin-inducible promoter, ethylene-inducible promoter, heat-shock promoter, seed storage protein promoter.

Non-limiting examples of yeast promoters include: 3-phosphoglycerate kinase promoter, glyceraldehyde-3-phosphate dehydrogenase (GAPDH) promoter, galactokinase (GALI) promoter, galactoepimerase promoter, and alcohol dehyderogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

The present invention further relates to a method of altering the physical properties of a plant cell wall or any product containing plant cell walls, such as for example paper or textile. Given its properties to affect the plant cell wall, β-expansins of the invention find use in a number of industries. For example, β-expansins can be used in the paper industry for paper recycling.

The paper products industry employs ¾ million workers and is a $60-billion industry in the U.S. alone (plus $40 billion in retail sales). Recycling is a growing concern and will prove more important as the nation's landfill sites become more scarce and more expensive.

The advantages of using expansins for paper recycling include the following: the protein is nontoxic and environmentally innocuous; it could substitute for current harsh chemical treatments which are environmentally noxious. The protein is effective on paper products which are now recalcitrant to current recycling processes. Its use could expand the range of recyclable papers. Because the protein acts at moderate temperature and in mild chemical environments, degradation of paper fibers during recycling should be reduced. This should allow for recycled paper fibers with stronger mechanical properties and with the ability to be recycled more often than is currently practical. Moreover, savings in energy costs associated with heating and beating the paper may be realized.

Other modes of application of β-expansins include production of virgin paper. Pulp for virgin paper is made by disrupting the bonding between plant fibers. Beta-expansins may be useful in the production of paper pulp from plant tissues. Use of expansins could substitute for harsher chemicals now in use and thereby reduce the financial and environmental costs associated with disposing of these harsh chemicals. The use of expansins could also result in higher quality plant fibers because they would be less degraded than fibers currently obtained by harsher treatments.

Beta-expansins may be also used to make harsh plant fibers, such as wood fibers, accessible as a biomass source for alcohol production. To achieve this result, β-expansins may be added alone, or in combination with α-expansins, to an alcohol manufacturing process. Alternatively, a plant intended as a source for making alcohol may be transformed with the polynucleotides of the invention hence making a plant having softer fibers that are easier to process. Methods for introducing polynucleotides of the invention into plant cell, and regenerating plants therefrom are well known in the art and are described, for example, in: Plant Molecular Biology, Ed. R. R .D. Croy, Bios Scientific Publishers, Academic Press, 1993.

Beta-expansins of the invention may also be used to alter the growth behavior of plants transformed with a β-expansin encoding polynucleotide.

Figure 6:
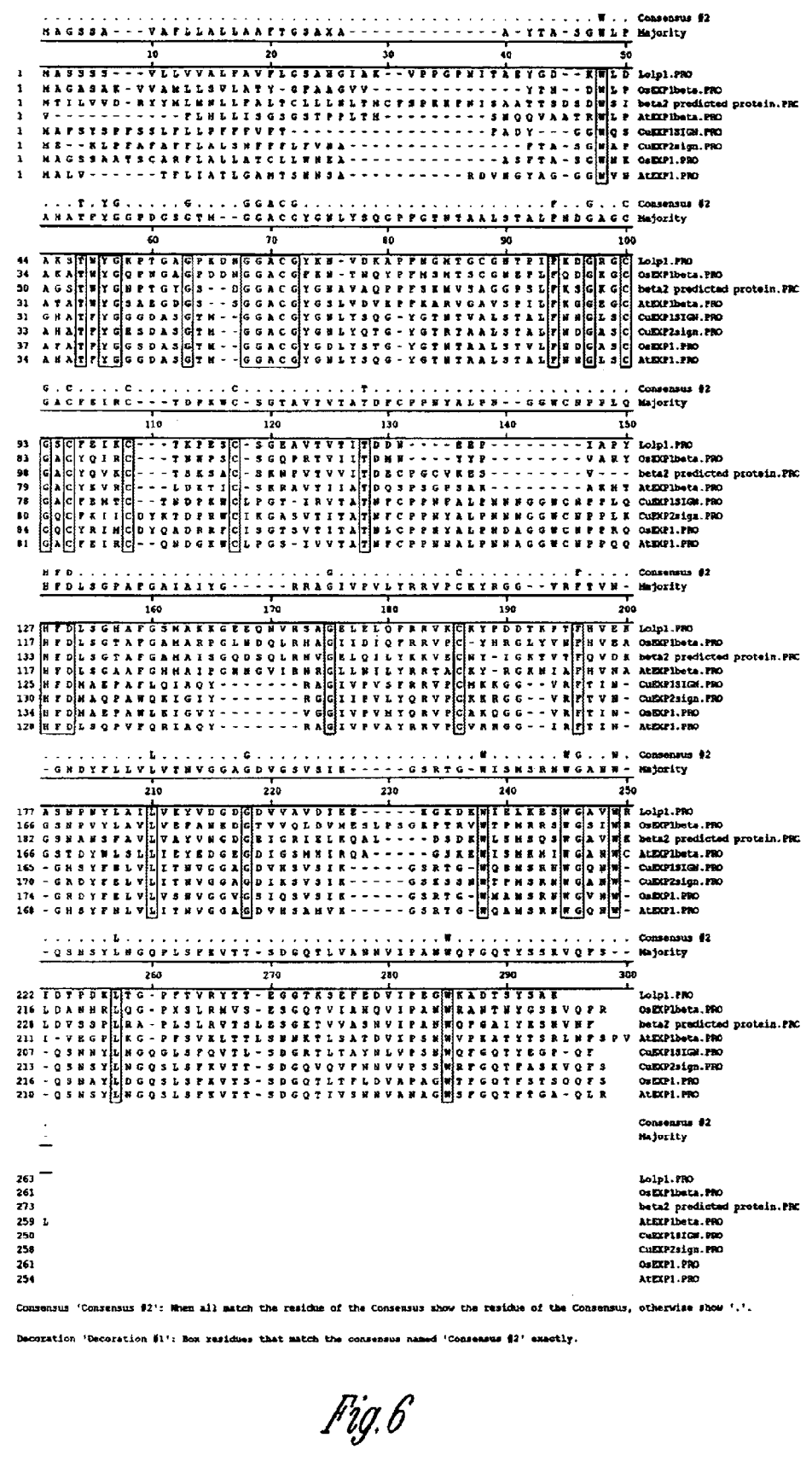

In another embodiment, the invention relates to a method for identifying, isolating and purifying the β and α-expansins of the invention. The method is based on the findings described herein that β and α-expansins contain conserved sequences as shown in FIGS. 5 and 6. New expansins may be identified by assaying crude extracts of plant, fungal, or other origin for their ability to induce extension (creep) of cell walls from plants. Suitable plant walls materials include, but are not limited to, frozen/thawed/heat-inactivated specimens from cucumber hypocotyls or grass coleoptiles clamped under tension in an extensometer and incubated in an acidic buffer, such as 50 mM sodium acetate, pH 4.5. Active extracts may be further purified by combining extensometer assays with protein fractionation techniques such as HPLC, electrophoresis, and selective precipitation with ammonium sulfate, polyethylene glycol, antibodies, and other affinity matrices. In this way, new proteins with expansin activity may be identified and purified. New expansin genes may be cloned in many standard ways, such as the use of polymerase chain reaction (PCR) to amplify gene fragments or cDNA fragments, using primers based on the conserved amino acid residues shown in FIGS. 5 and 6. Alternatively, cDNA and genomic libraries made from plants, fungi or other biological materials may be synthesized and screened at low stringency (e.g. hybridization and washing in 3X SSC at 50° C. using a nucleotide sequence encoding the conserved parts of the expansin protein).

The invention is further described in the following non-limiting examples.

EXAMPLES

Example 1

Protein Structure Analysis. Dot plots were calculated with Antheprot (McQueen-Mason, S. et al., (1988) CABIOS 5:159–160), using the unity matrix, a window size of 15 and a similarity threshold of 10. Secondary structure predictions were made with the pro-rum PHD via its mail server (Rost, B. (1996) *Meth. Enzymol.* 226:524–539). Hydrophobic cluster analysis used the program PCHCA (B. Boutherin, S. Lavaitte, B. Henrissat; Centre de Recherches sur les Macromolécules Végétales, CNRS, Grenoble, France) to make the initial two dimensional map and standard techniques to identify clusters (Henrissat, B., et al., (1995) *Proc. Natl. Acad. Sci. USA* 92:7090–7094; Lemesle-Varloot, L., et al., (1990) Biochimie 72:555–574).

Protein Extraction, Purification and Analysis. Pollen from greenhouse-grown *Zea mays* L. plants was collected daily, sifted to remove debris, and frozen at −80 C. Twenty g of pollen was thawed, extracted at 4 C for 1 h in 80 mL 0.125 M $NaCO_3$, centrifuged to remove pollen debris, and the supernatant was dialyzed against 10 mM sodium acetate, pH 5.5 or 4.5. Prior to rheology assays, the extract was typically diluted with 4 volumes of 50 mM sodium acetate and adjusted to pH 4.5.

For purification, pollen extract was prepared as above without the dialysis step and desalted on a Bio-Gel P-10 column pre-equilibrated with 10 mM MES, pH 6.0. The desalted fraction was brought to 60 mM NaCl, and 5 mL (typically 5–10 mg protein per mL) was loaded onto a 2-mL CM-Sepharose column pre-equilibrated with 60 mM NaCL.10 mM MES, pH 6.0. Protein was eluted with a pH gradient and salt steps (0–10 min: isocratic in 60 mM NaCl, 10 mM MES, pH 6.0; 10–75 min: continuous gradient to 60 mM NaCl, 10 mM HEPES. pH 8.5:75–100 min: NaCl increased in steps to 70 mM, 90 mM, 110 mM, and 220 mM (in 10 mM HEPES, pH 8.5). Fractions were desalted on a 10-kD or 30-kD Centricon microconcentrator prior to further testing.

Proteins were quantified calorimetrically with Coomassie Protein Assay Reagent (Pierce, Rockford, Ill.) and analyzed by 15% SDS-PAGE and western blots using standard procedures (Li, Z.-C., et al. (1993) *Planta* 191:349–356). Gels were electroblotted onto nitrocellulose membrane and blocked with 10% horse serum in phosphate-buffered saline containing 0.05% Tween-20. To detect expansins, rabbit polyclonal antibody raised against purified cucumber "S1" expansin protein (Li 1993) was used at 1,000:1 dilution and subsequently detected using goat anti-rabbit IgG-conjugated alkaline phosphatase. Mouse monoclonal antibody against Lol pI(4) was used at 5,000:1 dilution to detect group I allergens.

Rheology Assays. Maize silks were obtained from greenhouse-grown plants; coleoptiles of wheat (*Triticum aestivum* L., cv. Pennbar) and hypocotyls of cucumber (*Cucumis sativus* L., cv. Burpee Pickler) were obtained from 4- to 5-day-old etiolated seedlings germinated in moist vermiculite (Cosgrove, D. J. (1989) *Planta* 177:121–130). For creep reconstitution experiments, 1-cm segments were cut from the apical growing region, frozen at −20 C, thawed, abraded with carborundum slurry, heat inactivated and clamped in constant-load extensometers, as described previously (Cosgrove 1989). To compensate for the varying thickness of the wall specimens, 5-g weights were used to keep the silk walls under constant tension, whereas 20-g weights were used for the coleoptile and hypocotyl walls. For the stress relaxation measurements, the walls were pretreated for 10 min in either buffer or maize pollen extract, then stored on ice prior to extension and stress-relaxation measurements (Cosgrove 1989). Maximal force equivalents for the stress relaxation assays were 5 for silks, 20 g for coleoptile and hypocotyls.

When GenBank and SwissProt databases were searched using the BLAST and FASTA programs (Altschul, S. F., et al., (1990) *J. Mol. Biol.* 215:403–410; Pearson, W. R. et al., (1988) *Proc. Natl Acad. Sci. USA* 85:2444–2448), the only protein sequences with significant similarity to expansins were the group I pollen allergens and their homologs. Dot plots and sequence alignments show that expansins (hereafter called α-expansins) and group I allergens have short regions of conservation distributed throughout most of the protein backbone (FIG. 1A); these consist, notably, of five stretches of 15 amino acids with 40 to 53% identity (identified with the nos. 1 to 5 in FIG. 1A). The domains conserved between the specific combination of α-expansin Cs-EXP1 and the pollen allergen Lol pI (FIG. 1A) are also highly conserved within both groups of proteins. Likewise, both groups of proteins have hydrophobic signal peptides at the amino termini, characteristic of secreted proteins. Overall, the proteins share only 20–25% amino acid identity.

Figure 1C:
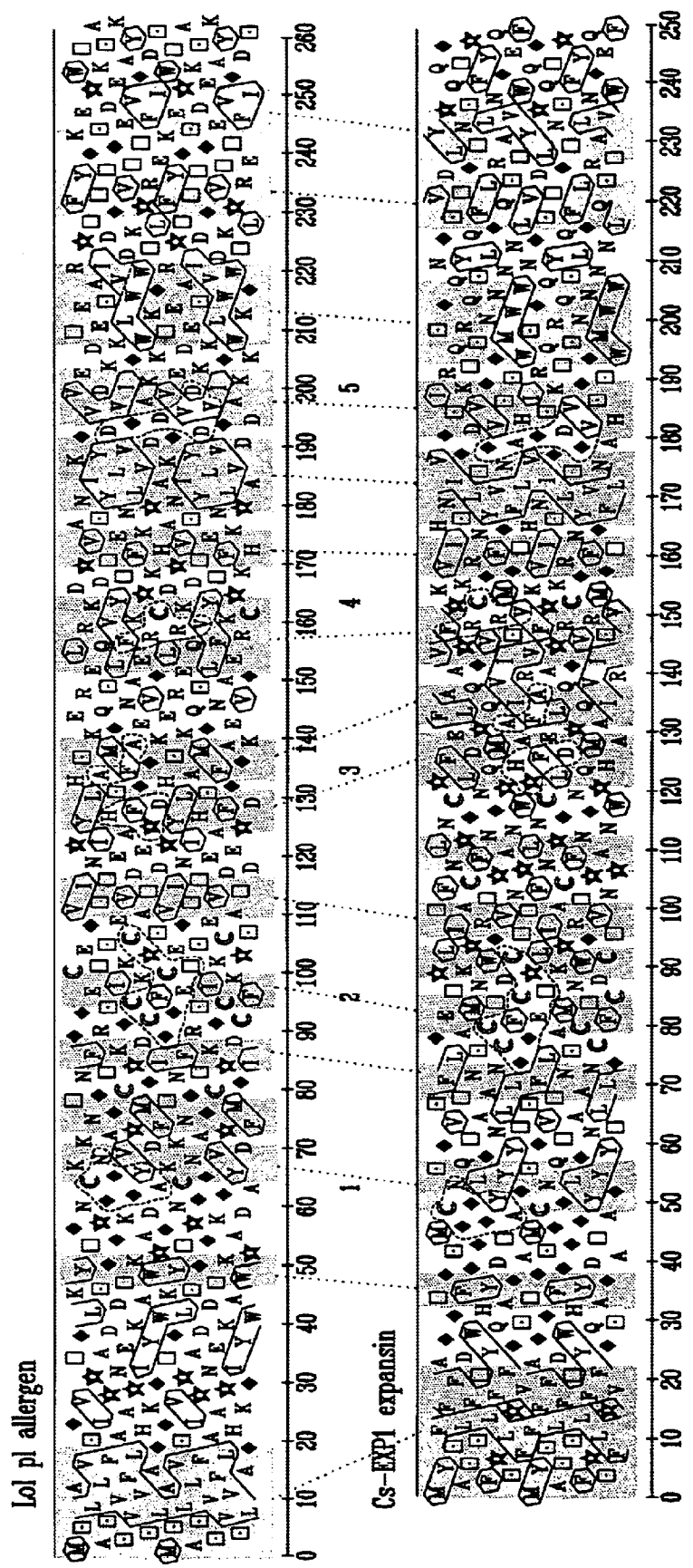

Despite this low sequence similarity, about 75% of the two proteins are predicted to have the same secondary structure, consisting mostly of loop regions (−60%), with a small proportion of α strand (−25%) and α helix (−15%) (FIG. 1B). These structural predictions were made with the PHDsec program (Rost, B. et al., (1994) *Proteins* 19:55–77; Rost, B. (1996) *Meth. Enznyol.* 226:524–539), using eight aligned group I allergens to predict the allergen structure and 11 aligned α-expansin homologs to predict the structure of α-expansion. While the accuracy of this prediction method is said to be better than that of other methods (Rost 1994), the important point to be made here is not that the predictions closely approximate the true structure of the proteins, but rather that the two predicted patterns closely resemble each other, despite the low sequence similarity. Likewise, the structural similarities between α-expansins and group I allergens is supported by hydrophobic cluster analysis (FIG. 1C). This method uses a two-dimensional display of amino acids to identify spatial patterns of hydrophobic residues and other motifs that correspond to secondary structure elements and is useful for recognizing related proteins with low sequence similarity (Henrissat 1995; Lemesle-Varloot 1990). Hydrophobic cluster analysis indicates that α-expansins and group I allergens are structurally congruent throughout most of their protein backbones. Six conserved cysteines can be identified, suggestive of a common patten of disulfide bond formation and protein folding. An additional cysteine pair that is strictly conserved in the α-expansins [cys-105 and cys-119 in Cs-EXP1] is missing in the pollen allergens. From the foregoing observations and similarities, Applicant hypothesized that group I allergens might have α-expansin-like biochemical activities.

Notwithstanding these structural similarities, α-expansins and group I allergens have notable differences in certain properties, suggestive of divergent biological functions. α-Expansin proteins are found in low abundance even in rapidly growing tissues where they are specifically expressed; they are not readily soluble in solutions of low ionic strength, are not glycosylated, and are tightly bound to cell walls (McQueen-Mason 1992; McQueen-Mason, S. et al., (1995) *Plant Physiol.* 107:87–100; Cosgrove, D. J. (1996) *BioEssays* 18:533–540.). In contrast, group I allergens are found in high abundance in pollen, are highly soluble in dilute solutions, are glycosylated, and apparently do not bind tightly to the pollen wall (Marsh, D. G. (1975) in *Allergens and the genetics of allergy*, ed. Sela, M. (Academic Press, New York), pp. 271–291; Knox, R. B., et al., (1993) in *Pollen allergens: botanical aspects*, eds. Kraft, D. L, Sehon, A. (CRC Press, Boca Raton), pp. 31–38). These differences suggest that the function of the group I allergens may be to loosen or expand the cell walls of the stigma and style to allow penetration of the pollen tube through these tissues. The grass pollen tube grows by tip growth to force its way between the tightly pressed cell walls of the stigma before entering the stylar track, where growth of the pollen tube involves further intrusive growth through and between cell walls (Heslop-Harrison, Y., et al., (1984) *Acta Bot. Neerl.* 33:81–99). Secretion of cell-wall loosening or expanding agents with expansin-like properties would presumably aid invasion of the pollen tube into the maternal tissues.

Example 2

Figure 2A:
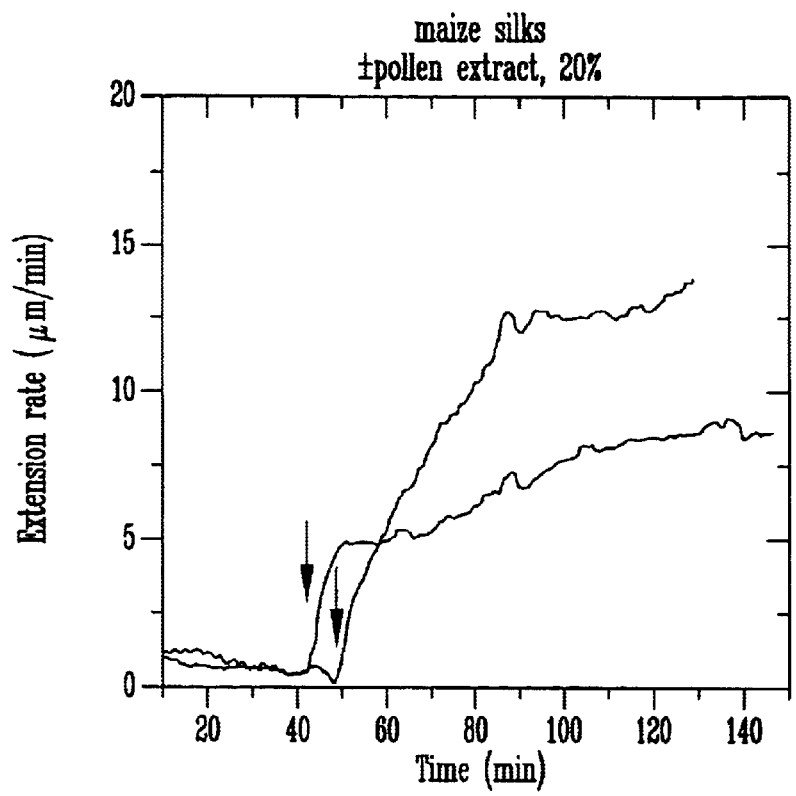
FIG. 2 shows enhancement of cell wall extension (top panels) and stress relaxation (bottom panels) by maize pollen extract. (A) and (B) show rheology responses of maize silk walls to pollen extract diluted to 20% strength (1:4 dilution with 50 mM acetate buffer, pH 4.5). (C) and (D) show responses of wheat coleoptile walls to 20% pollen extract. (E) and (F) show the modest responses of cucumber hypocotyl walls to undiluted (100%) pollen extract. For the extension assays, heat-inactivated wall specimens were clamped in a constant-load extensometer in 50 mM sodium acetate buffer, pH 4.5; wall extension (creep) was detected by a position transducer attached to one of the clamps and is plotted as extension rate. (McQueen-Mason, S. et al., (1992) *Plant Cell* 4:1425–1433; Cosgrove, D. J. (1989) *Planta* 177:121–130.) At the time indicated by the arrow, the buffer surrounding the wall specimen was exchanged for a similar one containing maize pollen extract. Extension traces show two representative results from 4 to 8 replicates. For the stress relaxation assays, heat-inactivated walls were pre-incubated in buffer +/− pollen extract, then clamped in an extensometer, extended to a predetermined load, and held at constant length during the subsequent relaxation (Cosgrove 1989) either in 50 mM acetate buffer (dotted lines) or the same buffer containing maize pollen extract at the dilution indicated. The decay in stress is plotted as a relaxation spectrum (log-time derivative of stress). Each relaxation curve is the average of 6–9 independent relaxation measurements.
Figure 2B:
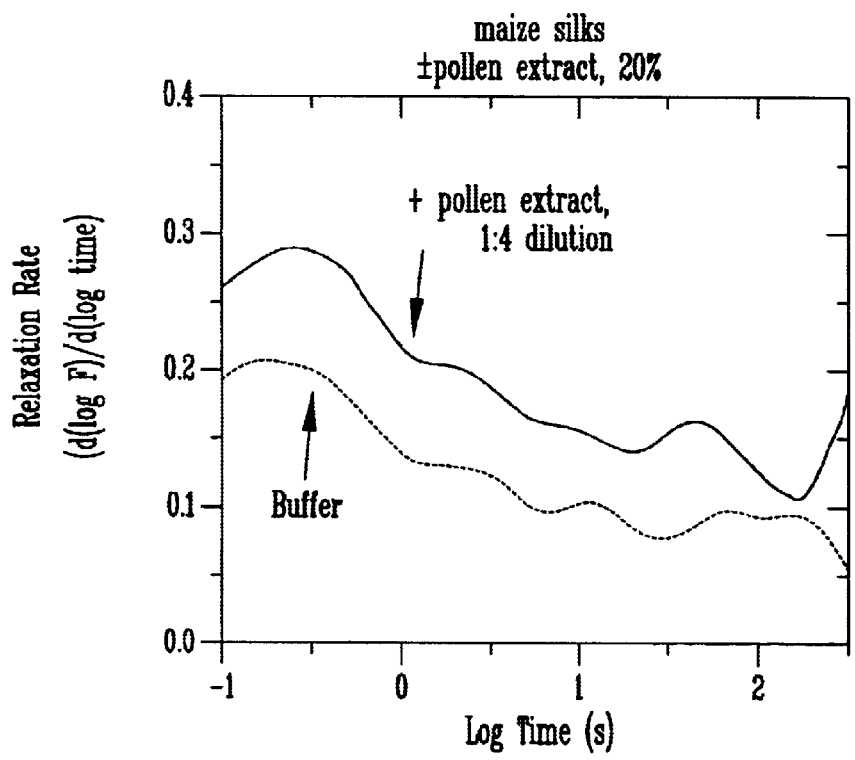

To test whether group I pollen allergens may loosen or expand cell walls, Applicant extracted protein from maize (*Zea mays*) pollen, which contains the group I allergen Zea mI (Broadwater, A. H., et al., (1993) *Gene* 131:227–230; Bedinuer, P. A., et al., (1994) in *Molecular Studies of pollen development in maize*, eds. Stephenson, A. G. & Kao, T.-h., (American Society of Plant Physiologists, Rockville, Md.), pp 1–14), and assayed its effects on the wall rheology of maize silks, which are the receptive stigmas and styles of the maize flower. Maize was used for these experiments because it is easy to collect large quantities of maize pollen and because the large size of the maize silk facilitates Theological assays. For these assays, silk walls were prepared so as to inactivate endogenous proteins and they were then clamped either at constant force to measure extension behavior or at constant extension to measure stress relaxation behavior (McQueen-Mason 1994; Li 1993). Addition of the maize pollen extract induced rapid, irreversible extension (creep) of the silk walls when tested in constant-force extensometers (FIG. 2A). Likewise, the pollen extract enhanced stress relaxation of the silk walls over a large range of times (FIG. 2B). Both of these Theological effects are unique characteristics of expansion action (McQueen-Mason 1992; McQueen-Mason 1995; Cosgrove 1996). Moreover, these rheological effects required an acidic pH (<5.5), likewise similar to the action of expansins. These results demonstrate that maize pollen can release a potent expansin-like activity. They also give direct support to suggestions that proteins secreted by pollen may alter the walls of receptive tissues (Wing, R. A. et al., (1990) *Plant Mol. Biol.* 14:17–28; Turcich, M. P., et al., (1993) *Plant Mol. Biol* 23:1061–1065; Mascarenhas, J. P., (1990) *Am. Rev. Plant Physiol. Plant Mol. Biol.* 41:317–338).

Despite its expansin-like activity and the limited amino acid similarity between the allergens and α-expansins, the pollen extract did not contain proteins recognized by anti-expansin antibodies (FIG. 3B). These antibodies recognize α-expansins of both dicot and monocots (Li 1993; Keller, E., et al., (1995) *Plant J.* 8:795–802; Wu. Y., et al., (1996) *Plant Physiol.* 111:765–772). Other properties also belie the possibility of a cryptic presence of an α-expansin in the pollen extract: The pollen activity was readily soluble in solutions of low ionic strength, whereas higher salt concentrations are needed to extract and maintain solubility of α-expansins. Concentrations of NaCl greater than 200 mM strongly inhibited the creep activity of the pollen extract, whereas at least two-fold higher concentrations were required to inhibit α-expansin activity. Microcrystalline cellulose (Avicel, 10 mg/mL) depletes α-expansin solutions of creep activity by binding α-expansins and removing them from solution (McQueen-Mason 1992; McQueen-Mason 1995), but this was not possible with the pollen activity. Applicant concludes therefore that the maize pollen extract does not contain a classical α-expansin protein.

Consistent with previous work (Broadwater 1993), the pollen extract did contain Zea mI, a group I allergen recognized by antibodies raised against the rye grass pollen allergen Lol pI (FIG. 3C). The pollen extract was fractionated on a carboxymethyl Sepharose column, and fractions were assayed by immunoblot, SDS-PAGE, and wall extension assays (FIGS. 3D–G). Fractions testing positive for group I allergens by immunoblotting possessed significant wall extension activity, whereas fractions testing negative in the immunoblot assay lacked expansin-like wall extension activity. A fraction highly purified for Zea mI (FIGS. 3E,F) tested positive in the wall extension assay (FIG. 3G). Applicant therefore concludes that Zea mI possesses expansin-like wall loosening or expanding activity.

Late-eluting fractions (i.e. at 80–95 min in FIG. 3D) also contained isoforms of Zea mI and exhibited potent creep activity (not shown), but they also contained additional proteins. Some pollen fractions caused sudden wall breakage (unlike expansins) or acted synergistically when added to pure Zea mI fractions (data not shown); these fractions may contain pectate lyases or other wall degradative enzymes (Turcich 1993; Mascarenhas 1990).

Figure 2C:
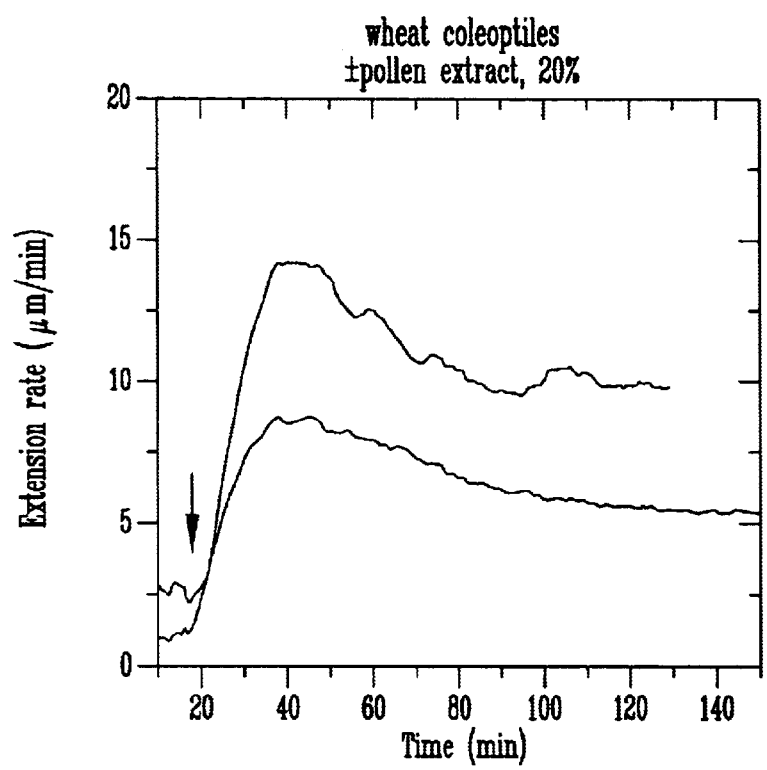
Figure 2D:
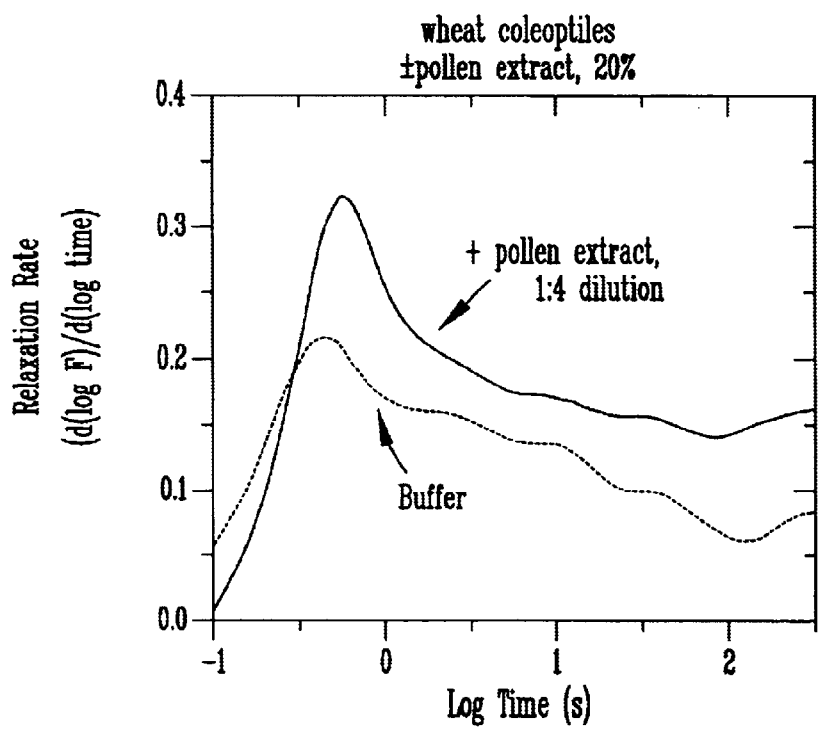
Figure 2E:
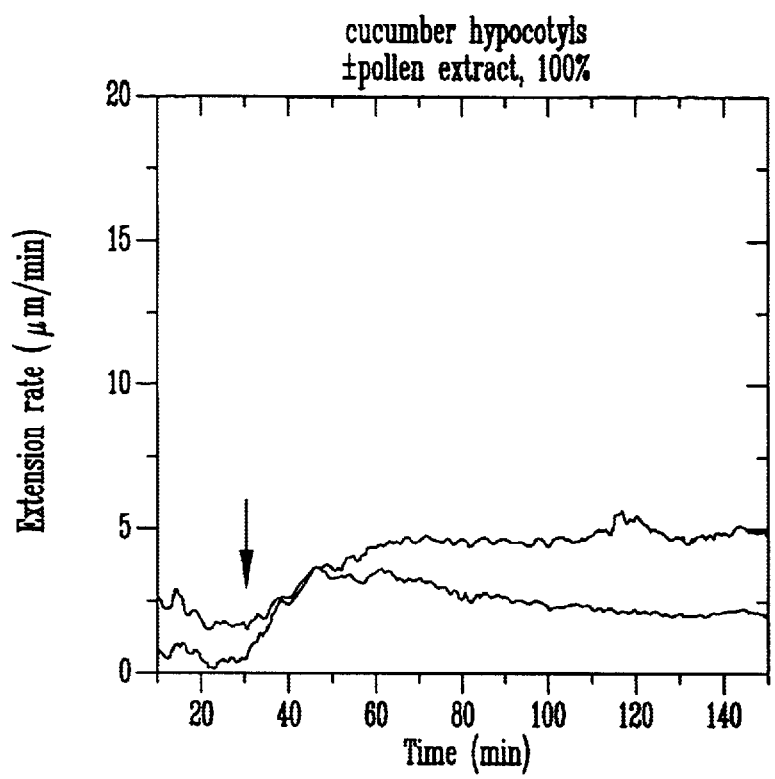
Figure 2F:
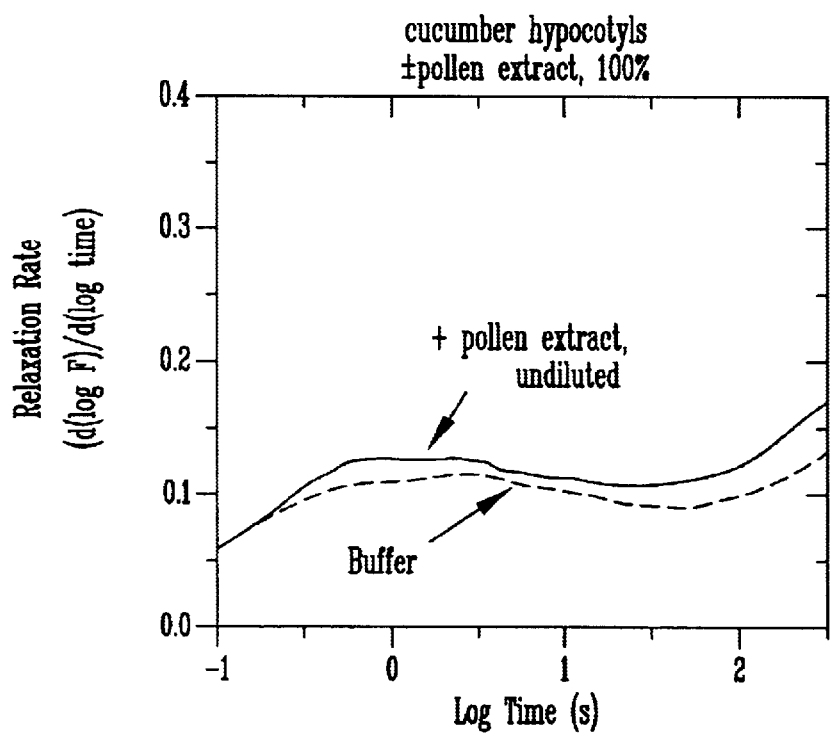

Further work showed that the maize pollen extract was more effective as a wall loosening or expanding agent with grass cell walls than with dicot cell walls. For example, the pollen extract had a marked effect on the creep (extension) and stress relaxation of coleoptile walls from young grass seedlings (FIGS. 2C, D), but its rheological effects on hypocotyl walls from cucumber seedlings were small. At the same concentration that proved very effective on grass walls (i.e. at 1:4 dilution), the pollen extract had a barely detectable effect on wall creep and stress relaxation of cucumber walls (data not shown). Even at 5-fold higher concentration (i.e., undiluted pollen extract), the activity seen using cucumber walls was only about one quarter the activity found using the 20% extract on grass walls (FIGS. 2E, F).

This selectivity for grass walls complements the action of α-expansins, which appear to induce creep more effectively in dicot walls than in grass coleoptile walls (McQueen-Mason 1992). Even though α-expansins are found in grass coleoptiles (Shcherban 1995), they proved more effective on dicot walls than on grass coleoptile walls, at least as assayed by reconstitution assays of wall creep (14).

Similar, though less extreme, results were found in creep reconstitution assays with wall specimens from maize roots (Wu 1996) and rice internodes (Cho, H.-T., et al., (1997) *Plant Physiol.* in press). In this context, it is notable that grass walls are unusual in composition, being relatively poor in pectins and xyloglucans and rich in glucuronoarabinoxylans and (1→3), (1→4)-α-D-glucans, when compared with walls of other angiosperms, including other monocots (Carpita, N. C., et al., (1993) *Plant Journal* 3:1–30). It seems likely that α-expansins and Zea mI act on different components of the wall, which may differ in abundance and in their role in wall mechanics in dicots versus grasses. Additional insight into the functional significance of the Group I allergens and their homologs may be gained from analysis of the protein and DNA databases. Group I allergens have been identified in the pollen of many grass species (Smith, P. M., et al., (1994) *Mol. Inununol.* 31:491–498), but not in pollen of species outside the grass family, including ragweed and other species that elicit potent pollen allergies. Neither have they been identified in monocots outside the grass family. Applicant tested pollen extracts from petunia (a dicot) and lily (a monocot, but not a grass) for wall extension activity, with negative results. These observations suggest that grasses may be unique in expressing high levels of these wall-loosening or expanding proteins in pollen.

Example 3

An analysis of the rice and Arabidopsis cDNA databases shows that expression of this gene family is not limited to pollen. The rice EST (Expressed Sequence Tag) collection currently contains 18 partially sequenced cDNA entries that are close homologs to the group I pollen allergens (e.g., long stretches with 60% identity and 80% similarity at the amino acid between Lol pI and the rice EST homologs). The 18 cDNAs fall into 7 distinct sequence classes, represented by Genbank accession numbers D41180, D24261, D46769, D39144, D24972, D40180, D48180. As they are, all expressed in young seedlings without flowers, these cDNAs cannot be from pollen, and so they are referred to as vegetative homologs of the group I allergens. The Arabidopsis EST collection currently contains at least 1 homolog of the pollen allergens (Genbank accession number Z37641), which is likewise expressed in young seedlings without flowers. Additionally, cim1, a cytokinin-induced gene expressed in soybean cell cultures (Crowell, D. N. (1994) *Plant Mol. Biol.* 25:829–835), is also a vegetative homolog of the group I allergens. Vegetative homolog of the group I allergens from the rice and Arabidopsis EST collections were sequenced. These sequences were used together with related sequences in Genbank, to construct a phylogenetic tree for α-expansins and group I allergens (FIG. 4). The tree shows two deeply branched families, with the vegetative homologs of the group I allergens occupying a position intermediate between the group I allergens and α-expansins. Because α-expansins and group I allergens have wall-loosening or expanding activity, the vegetative homologs of the group I allergens are also expected to possess expansin-like properties.

To test this idea, an attempt was made to identify the vegetative homologs of group I allergens by western blots of wall proteins extracted from grass seedlings using monoclonal antibody directed against Lol pl, but without success (not shown). This is consistent with previous results (Bedinuer 1994) and likely indicates that the major antigenic determinants of the group I pollen allergens are not conserved in their vegetative homologs. Our attempts to express recombinant expansins and group I allergens in *E. coli* have so far failed to result in active protein, evidently because of faulty disulfide bond formation (unpublished results of M. Shleh and D. J. Cosgrove). Thus, it remains to be seen how the activity of the vegetative homologs of the allergens compares with the pollen allergens and with α-expansins.

The experimental results reported here, as well as the database observations, suggest that the group I grass pollen allergens and their homologs in vegetative tissues constitute a second multi-gene family of expansins that function as wall loosening or expanding agents in plants, preferably in angiosperms. It is proposed that this family be referred to as beta-expansins, and the original family of expansins henceforth be referred to as α-expansins. The two families of expansins exert similar biophysical effects on the wall (i.e., they induce prolonged creep and stress relaxation in a pH-dependent manner), but apparently they interact with different components of the wall. The limited sequence similarity between these two families of expansins gives obvious targets for future studies of active sites and functional domains in these proteins.

In the grasses, the group I pollen allergens represent a subset of the beta-expansin family that appears to have assumed a specialized role during pollination, most likely for wall loosening or expanding of the maternal tissues for rapid pollen tube penetration. This idea is directly supported by our results, which show that these proteins have potent rheological effects on the walls of the grass stigma and style, where they are naturally released in abundance by the grass pollen. An additional possibility is that group I allergens are involved in pollen tube, where surface expansion occurs.

Determination of the in-vivo functions of beta-expansins in vegetative tissues will require further work. A potential wall-loosening or expanding role for the beta-expansin cim1 is consistent with induction of its expression by cytokinin (Crowell 1994), which stimulates cell proliferation and growth in soybean cell cultures. The large number of distinct beta-expansins expressed in rice seedlings suggest that beta-expansins have assumed multiple roles in grass seedling development, perhaps as agents controlling different types of cell growth, wall dissolution and separation, or other processes where wall pliancy is important.

Example 4

The beta-expansin gene may be isolated from any plant genomic DNA by (i) obtaining a beta-expansin gene fragment using the polymerase chain reaction (PCR) with a series of degenerative primers directed against the 5' and 3' regions of the beta-expansin sequence; and (ii) screening the plant genomic library with the obtained gene fragment as a primer to identify and isolate the full length gene. Degenerative primers can be based on conserved sequences represented in FIG. 5, such as for example regions TWYG, GGACG (SEQ ID NO:34), HFDLSG (SEQ ID NO:35) and HFD. This experimental approach can also be used with a plant cDNA library.

The genomic DNA (10 ng) may be amplified in a 100 μl reaction containing for example: 10 mM Tris-HCl pH 8.3, 1.5 mM $MgCl_2$, 500 mM KCl, 2.5 U Taq polymerase (Beohringer-Mannheim), 0.2 mM dNTPs and oligonucleotide primers (1 μM each) specific for beta-expansin sequences. PCR may be performed in an Omnigene thermocycler or any other available thermocycler. Amplification condition are generally known and can be optimized using routine experimentation. Other protocols for amplification may be used and are well known to persons of skill in the art. For example, protocols described in U.S. Pat. Nos. 4,683, 195, 4,683,202 and 4,800,159, and in Innis et al., PCR Protocols, Academic Press, Inc., San Diego Calif., 1990 (each of which is incorporated herein by reference in its entirety) may be used.

The amplification products containing beta-expansin polynucleotides may be gel-purified and ligated into any vector, for example into a pGEM vector. *E. coli* may be transformed with derived recombinant plasmids and cultured overnight at room temperature. Plasmid DNA may be isolated to prepare a probe for screening a cDNA or genomic library using standard methods described in, for example, Sambrook et al., Molecular Cloning, A Laboratory Manual, Second Edition, Cold Spring Harbor Laboratory Press, 1989, incorporated herein by reference.

The isolated DNA clone may then be used as a hybridization probe to recover the entire beta-expansin gene from a cosmid or lambda genomic library. The libraries may be prepared according to the methods well known in the art and described in Sambrook et al. The above-described procedure can be followed to isolate beta-expansin genes from any plant species. Furthermore based on the conserved regions represented in FIG. 6 (for example regions GGACG (SEQ ID NO: 34 and HFD), degenerative nucleotides may be constructed and the above procedure may be used to identify and isolate genes encoding alpha-expansins.

Applicant gratefully acknowledges technical assistance from Melva Perich, Carol Volk and Esther Polevoy, antibodies from D. G. Klapper, maize pollen and silks from D. Knelvel, EST clones from Dr. T. Desprez (INRA) of the French Arabidopsis EST project and Dr. Y. Nagamura of the Rice Genome Research Project, and the PCHCA program from B. Henrissat.

What is claimed is:

1. A composition comprising a beta-expansin or a fragment thereof, said composition having a property of inducing expansion or stress relaxation of plant cell wall material wherein said beta-expansin comprises an amino acid sequence having at least 90% sequence similarity as compared to the full length of SEQ ID NO:9, said beta-expansin further having one or more functional characteristics of beta-expansins wherein said characteristics are inducing expansion or stress relaxation on grass cell walls more effectively than on dicotyledon cell walls as determined by cell wall extension and stress relaxation assays.

2. The composition of claim 1, wherein said beta-expansin has a molecular weight from about 24 kDa to about 35 kDa.

3. The composition of claim 1, wherein said beta-expansin comprises conserved amino acids as shown in FIG. 5, when the amino acid sequence of said beta-expansin is aligned with the amino acid sequence of SEQ ID NO:9 using Clustal alignment algorithm.

4. The composition of claim 1, wherein said beta-expansin is a vegetative homolog of a class I pollen allergen.

5. The composition of claim 1, wherein said beta-expansin comprises a function-conservative variant of an amino acid sequence having at least 90% sequence similarity with said amino acid sequence as compared to the full length of SEQ ID NO.9.

6. The composition of claim 1, wherein said composition contains an acid buffer medium comprising acetate, citrate, or a combination thereof.

7. The composition of claim 1, having a pH from about 3.0 to about 5.5.

8. A composition comprising: a beta-expansin or fragment thereof wherein said beta-expansin comprises an amino acid sequence having at least 90% sequence similarity as compared to the full length of SEQ NO:9; and wherein said composition is capable of inducing expansion or stress relaxation of plant wall cells material and wherein said expansion or stress relaxation is more effective for grass wall cells as compared to dicotyledon plant wall cells, and wherein said expansion or stress relaxation is determined by induction of cell wall extension (creep) and/or an increase in the stress relaxation spectrum.

9. The composition of claim 1 wherein said beta-expansin is determined using an assay including, but not limited to, cell wall extension and stress relaxation assays wherein said assays demonstrate said characteristics specific to beta-expansins.

10. A composition of claim 1, wherein said beta-expansin or a fragment thereof comprises one or more functional characteristics of beta-expansins such as inducing expansion or stress relaxation of plant cell walls as determined by cell wall extension and stress relaxation assays.

11. A composition of claim 1, wherein said beta-expansin or a fragment thereof comprises the functional characteristic of inducing expansion or stress relaxation more effectively on grass cell walls than on dicoyledon cell walls as determined by cell wall extension and stress relaxation assays.

* * * * *

UNITED STATES PATENT AND TRADEMARK OFFICE
CERTIFICATE OF CORRECTION

PATENT NO. : 6,682,738 B1 Page 1 of 1
APPLICATION NO. : 09/071252
DATED : January 27, 2004
INVENTOR(S) : Daniel J. Cosgrove It is certified that error appears in the above-identified patent and that said Letters Patent is hereby corrected as shown below:

Column 1, lines 9-12

DELETE:
    "This research was supported by the grants MCB9317864 from the US National Science Foundation. The United States Government may have some rights in this invention."

ADD:

--This invention was made with government support under Grant No. MCB9317864, awarded by the National Science Foundation. The Government has certain rights in the invention.--

Signed and Sealed this

Nineteenth Day of October, 2010

David J. Kappos
*Director of the United States Patent and Trademark Office*

SEQUENCE LISTING

<160> NUMBER OF SEQ ID NOS: 37

<210> SEQ ID NO 1
<211> LENGTH: 780
<212> TYPE: DNA
<213> ORGANISM: Arabidopsis

<400> SEQUENCE: 1

```
gtcttcctcc accttctaat aagtggctct ggctctactc caccgttgac tcactccaat      60
caacaagtgg cagccactcg ttggcttccc gccaccgcaa cctggtacgg aagtgccgag     120
ggagacggca gcagcggagg agcttgtggt tacggatcgt tggtggacgt gaagccgttt     180
aaggctagag tcggagcggt gagtccgatt ctgttcaaag gtggtgaagg ctgcggtgca     240
tgctacaagg tcaggtgtct cgacaagacc atttgctcta agagagcagt caccattatt     300
gccaccgacc agtcaccgtc aggaccatct gctaaagcaa aacacactca tttcgacctc     360
agtggcgccg cctttggaca tatgctatt  cccggccata acggtgtcat ccgcaaccgt     420
ggcctattaa acatcctcta ccgccgaacg gcatgcaaat acagagggaa gaacatagcg     480
tttcatgtga acgcaggatc aactgattat tggttatcgc ttctcattga gtatgaagac     540
ggtgaaggag acattggctc tatgcacatt cgtcaagcgg gatctaagga gtggatatcg     600
atgaagcaca tatggggagc gaactggtgc atcgtcgaag gaccactcaa gggaccattc     660
tccgtgaagc tcacaacttt gtccaacaat aagacactct ccgccaccga cgtcatcccc     720
agtaactggg ttcccaaagc tacttacacc tctcgcctca acttctcccc tgttctctaa     780
```

<210> SEQ ID NO 2
<211> LENGTH: 999
<212> TYPE: DNA
<213> ORGANISM: Oryza sativa

<400> SEQUENCE: 2

```
cccacgcgtc cgagcagaca aggtagtagt acaggctttt gtacgtacgt agcagaggga      60
gttcccaaga tggctggggc ctctgccaag gtcgtcgcga tgctgctctc cgtgctcgcc     120
acgtacggct tcgccgccgg cgtcgtctac accaacgact ggctcccggc caaggccacc     180
tggtacggcc agcccaacgg cgccggaccc gacgacaacg gcggtgcgtg cgggttcaag     240
aacaccaacc agtacccgtt catgtccatg acctcctgcg gcaacgagcc tctgttccag     300
gacggcaagg gctgtggcgc ctgctaccag atacggtgca ccaacaaccc gtcgtgctcc     360
gggcagccca ggacggtgat catcacggac atgaactact accccgtggc caggtaccac     420
ttcgacctga gcggcacggc gttcggcgcc atggcgaggc cggggctgaa cgaccagctc     480
cgccacgccg gcatcatcga catccagttc aggcgcgtcc cgtgctacca ccgcggcctc     540
tacgtgaact tccacgtcga ggccgggtcc aacccggtgt acctcgccgt gctggtggag     600
ttcgccaaca aggacggcac ggtggtgcag ctcgacgtca tggagtcgct ccccagcggc     660
aagccgacgc gggtctggac gcccatgcgc cgctcctggg gatccatctg cgcctcgac      720
gccaaccacc gcctccaggg cccctmtcc  ctccgcatgg tcagcgagtc cggccagacc     780
gtcatcgccc accaggtcat cccggccaac tggagggcca acaccaacta cggctccaaa     840
gtccagttcc gttgatccat cgatcgatct acctatgtgc atgcaatgcc ttcgtcgtct     900
tgtgtcgccg gtcaagaacg aatttttgatt ctaccgatcg gcagttcggc actagtactg     960
tactacgatt ctgtgtgtgt gtgtgtgtgt gtgtgattg                            999
```

<210> SEQ ID NO 3
<211> LENGTH: 1004
<212> TYPE: DNA
<213> ORGANISM: Oryza sativa

<400> SEQUENCE: 3

| | | | | | |
|---|---|---|---|---|---|
| acgcgcttat | acgatcatat | aggcgaatgg | gtacgggccc | cctcgaggt | cgacccacgc | 60 |
| gtccgcggtg | atgtagaggt | agtagtgtac | tacctgctgc | tagtattagt | ggtggtgcag | 120 |
| gggtgcaaag | gcagcagcgc | ggtgcaggt | gaaggtcggt | ggtacaacga | gagcgaggcc | 180 |
| atcggtggtg | cggcggcgtg | ggggaacgcg | aaggcgacgt | ggtacgggca | gccgaacggc | 240 |
| gccggggcgg | cggacaacgg | cggggcgtgc | gggttcaaga | aggtgaacca | gtacccgttc | 300 |
| atggggatga | cgtcgtgcgg | gaaccasccg | ctgtacaagg | gcggcaaggg | ctgcggctcc | 360 |
| tgctaccgcg | tcaggtgcaa | tcgaaacccc | gcctgctccg | gcaacgccca | gaccgtcgcc | 420 |
| atcamcgaca | tgaactactt | ccccctctcc | cagtaccact | tcgacctcag | cggcatcgcc | 480 |
| ttcggccgcc | tcgccaagcc | cggccgcgcc | gacgacctcc | gccgcgcggg | gatcatcgac | 540 |
| gtgcagttcg | cgcgcgtgcc | gtgcgagttc | ccgggcctca | agtgggatt | ccacgtggag | 600 |
| gaagggtcca | gccccgtgta | cctggcggtg | ctggtggagt | acgagaacgg | cgacggagac | 660 |
| gtggcgcagg | tggacctcaa | ggaggccggc | gccggaggag | gaaggtggac | gccgatgcgg | 720 |
| gagtcgtggg | ggtcggtgtg | gaggctggac | tccaaccacc | gctgcgggc | gccattctcc | 780 |
| atccgcatcc | ggagcgactc | cggcaagacg | ttggtggcac | ccgacgtcat | cccctcaac | 840 |
| tggacgccca | acaccttcta | ccgttccttc | gtccagtact | cctcctagct | agctactcct | 900 |
| atacccatta | attyttccct | aattattcct | tcttgttatt | atattctacc | cttatatata | 960 |
| tatatatata | tgttattaaa | aaaaaaaaaa | aaaaaaaaaa | aaaa | | 1004 |

<210> SEQ ID NO 4
<211> LENGTH: 1378
<212> TYPE: DNA
<213> ORGANISM: Oryza sativa
<220> FEATURE:
<223> OTHER INFORMATION: unknown (1219)..(1376)

<400> SEQUENCE: 4

| | | | | | |
|---|---|---|---|---|---|
| gacgcgctat | agatcatata | ggcgaatggg | tacgggcccc | cctcgaggtc | gacccacgcg | 60 |
| tccgaagctc | agaatcctac | ctgactagta | ctaccactac | tagctagtag | cgagctactc | 120 |
| tctctggtca | tcaagctttg | agtggttgga | gtggtggcag | ctatggcttt | ttccatctcc | 180 |
| aagaaggctg | cagttgctgc | actcttctcc | ttccttgttg | tcacctgcgt | cgccggcgcc | 240 |
| aggccgggga | acttcagcgc | ctccgacttc | accgccgatc | ccaactggga | agtcgccagg | 300 |
| gccacctggt | acgcgctcc | caccggcgcc | ggccctgacg | acgatggcgg | tgcttgcggg | 360 |
| ttcaagaaca | ccaaccagta | cccgttctcg | tcgatgacct | cctgcggcaa | cgagcctatc | 420 |
| ttcaaggacg | ggaagggctg | tggctcatgc | taccagataa | gatgcgtcaa | ccaccctgcc | 480 |
| tgctccggca | acccggagac | ggtgatcatc | accgacatga | actatacccg | tttccaagta | 540 |
| cacttcgacc | tgagcggcac | ggcgttcggc | gccatggcca | agccggggca | gaacgaccag | 600 |
| ctccgccacg | ccggcatcat | cgacatccag | ttcaagaggg | tgccgtgcaa | cttccctggg | 660 |
| ctgaaggtga | cgttccacgt | ggaggagggg | tcgaacccgg | tgtacttcgc | ggtgctggtt | 720 |
| gagtacgagg | acggcgacgg | cgacgtggtg | caggtggatc | tcatggaggc | caactcccag | 780 |

-continued

```
tcgtggacgc cgatgcgcga gtcgtgggggc tccatctgga ggctcgactc caaccaccgc    840
ctcacggcgc ccttctcgct ccgcatcacc aacgagtccg gcaagcagct cgtcgccagc    900
caggtcatcc cggccaactg gcccccatg  gccgtctacc gttctttcgt ccagtacagc    960
agctaagcca atgatcaaga caagcataa  ttcatgccta ctatagcagc agcagaagca   1020
gcattagcta ctatacatac ctctacgtac gacatttgag atcgatcgtt tggccatttt   1080
tatctgctcg ggtattgatt agctctccct cggtattgtt atggatttgc atggatggtt   1140
cattaatctg tcatcaggag ttcgttttga gtaggtgaga cgtcggttgt tgggtgtcat   1200
atagacatcg ctcggtgtnt tgaggttgag agtgggataa ggaggaggca aagtttgcat   1260
gtgctgtccc gcccactctc actgtaccag tgtcactgtt tgtgtaacca gaacaaaggt   1320
cataaattat actantagta tacagtttgc tgcctggcna aaaaaaaan aaaaanaa     1378
```

<210> SEQ ID NO 5
<211> LENGTH: 1392
<212> TYPE: DNA
<213> ORGANISM: Oryza sativa
<220> FEATURE:
<223> OTHER INFORMATION: unknown (509)..(785)

<400> SEQUENCE: 5

```
gacgcgcgtt aatacgatca tatagggcga attgggtacg ggccccccct cgaggtcgac     60
ccacgcgtcc gcaccgccac ctctctcatc ggatccctgc araggargag agggcagtgg    120
cggcgaaagg cgacatgggc tcgctgtcct ctctcgccgc cgcggcggtg tttctctccc    180
tcctcgccgt cggccactgc gccgccgccg acttcaacgc caccgaygcc gacgccgact    240
tcgccggcaa cggcgtggac ttcaactcca gcgacgccgc cgtctactgg ggcccctgga    300
ccaaggccag ggccacctgg tacggccagc caacggcgc  cggccccgac gacaacggcg    360
gcgcgtgcgg gttcaagcac accaaccagt acccgttcat gtcgatgacc tcctgcggca    420
accagccatt gttcaaggac ggcaagggat gcggctcttg ctacaagatc agatgcacca    480
aggaccagtc ctgctccggc aggtcggana cggtgatcat caccgacatg aactactwmc    540
cggtggctcc gttccacttc gacctcagcg gcacggcgtt cggcaggctc gccaascytg    600
gcctcaacga caagctgcgc cactccggca tcatcgacat cgakttcacc arggtgccat    660
gcgagttccc ggggctcaag atcgggttcc acgtggagga gtactcgaac cctgtgtact    720
tcgcggtgct ggtggagtac naggacgcg  acggcgacgt ggtgcaggtg gacctgatgg    780
agtcnaaacg gcgcacgggc cgccgacggg ggaggtggac gccgatgagg gagtcgtggg    840
gstccatctg gaggctggac accaaccaca ggctccaggc ccccttytcc atccgcatcc    900
gcaacgagtc cggcaagacg ytygtcgcca acaacgtcat cccggccaac tggaggccca    960
acacattyta ccgctccttc gtccagtaca gctgaaccgc cgctcgccgg cggcgaccct   1020
cggcgccggc atccgcgccg ctgctgctgc tagtaatact actactgcta tgatgtaatt   1080
gtgttaccgg ttgggttytt tgagtttgtt ggggttgggg attgtgtggt cggtctgtgt   1140
tgcgatttgc agaaaccggg cgarcgaaag aagaaaaaaa aagctgtktk ggaaatggag   1200
gaggtaggcg tacaaggtta cgctttcccg cccactttcg cttttataat ttatcatttt   1260
caaatggtga tgatatgatg attaatcaaa aggattatat tgctaaaaaa aaaaaaaaaa   1320
gggcggccgc caccgcggtg gagctccagc ttttgttccc tttagtgagg ttaattgcgc   1380
gcttgggtat ca                                                      1392
```

<210> SEQ ID NO 6
<211> LENGTH: 420
<212> TYPE: DNA
<213> ORGANISM: Oryza sativa
<220> FEATURE:
<223> OTHER INFORMATION: unknown (215)..(405)

<400> SEQUENCE: 6

| | | | | | |
|---|---|---|---|---|---|
| aatcccagct | acctaaccga | ttgcccaaca | agaaaatagc | aatggttagc | cggggcactt | 60 |
| tcgttttgc | cgtcctagtg | gcgctaccga | tactgtcact | ccccgtctct | ggctacgagc | 120 |
| agaactacac | tgccggcaga | cggagcacca | tgtcgctggg | cagaggctac | ggctggtcct | 180 |
| ccggcggcgc | gacgtggtac | ggcggcccgc | aaggngacgg | cagcgaaggt | ggcgcgtgcg | 240 |
| gttaccagag | cgccgtcggg | cagcgccgtt | tctcgtcgat | gatcgccgcc | gggggcccct | 300 |
| ccctcttcaa | gaatggcaaa | ggctgcggct | catgctacca | aattaagtgc | ancggcaacc | 360 |
| gggcgttctt | cggccgccag | tgaccgtcgt | gatcaacgac | ttctncctt | gagggggtatt | 420 |

<210> SEQ ID NO 7
<211> LENGTH: 357
<212> TYPE: DNA
<213> ORGANISM: Oryza sativa
<220> FEATURE:
<223> OTHER INFORMATION: unknown (274)..(340)

<400> SEQUENCE: 7

| | | | | | |
|---|---|---|---|---|---|
| tacttactac | cactactact | gctgctgctg | ccagttctag | ctagcctact | gctcttctcc | 60 |
| gagctgaaga | ttttcgagc | tagctaggat | ggcagccaga | atgggcagca | aggtcgctgc | 120 |
| aatcctcgcg | attctgtccg | tgctcgtggt | gcatggctct | tgcaaggggc | atcctgtgaa | 180 |
| ctacaacgtc | tccgacgcct | ccgcctacgg | ctccggctgg | ctccctgccc | gggcaacctg | 240 |
| gtatggcgct | cccaccggcg | ccggcccctga | cggnnacaac | ggcggcgctt | gcggggttca | 300 |
| agaacgtgaa | ccagtaccca | ttctcgtcca | tgacctcctn | cggaaacgag | cccattt | 357 |

<210> SEQ ID NO 8
<211> LENGTH: 819
<212> TYPE: DNA
<213> ORGANISM: Glycine max

<400> SEQUENCE: 8

| | | | | | |
|---|---|---|---|---|---|
| atgacaattc | ttgtcgtaga | tcgatactac | atgctcatga | acttactctt | tgctctaact | 60 |
| tgtctcctct | tgaacttaac | tcattgcttt | agccccaaga | aattcaacat | ttcagccgcc | 120 |
| acgaccagcg | attctgattg | gtctatcgcc | ggatctacgt | ggtatggtaa | ccccaccgga | 180 |
| tacggaagcg | acggtggagc | ttgtggttat | ggaaatgctg | ttgcacaacc | tccgttttcg | 240 |
| aaaatggtat | cagccggagg | tccgtcgttg | ttcaagtcag | gaaaaggatg | tggtgcatgt | 300 |
| taccaggtaa | aatgcacttc | gaaatcggca | tgttcgaaaa | atcctgttac | ggtggtcatt | 360 |
| acagatgaat | gtcctggatg | cgttaaggag | tcggtccatt | tcgatttgag | tggtacagcg | 420 |
| tttggtgcca | tggcaatttc | tggtcaagat | agtcagcttc | gcaatgtcgg | agaattgcag | 480 |
| attcttttata | aaaggttga | gtgcaactat | ataggcaaaa | cggtgacatt | tcaagtggat | 540 |
| aaaggttcaa | acgctaactc | cttcgcgtt | ttggttgcgt | atgtaaacgg | agacggcgaa | 600 |
| attggccgaa | ttgaactcaa | acaagctcta | gattctgaca | agtggttgtc | tatgagccaa | 660 |
| tcatggggcg | ccgtgtggaa | gctcgacgtg | tcgtcacctt | tgcgtgcccc | gctctctctc | 720 |
| cgagtgactt | cgttggaatc | cggcaagact | gttgtggctt | ccaatgtcat | tcccgcaaac | 780 |

```
tggcaacccg gtgcgatata caaatccaac gtcaacttt                   819
```

<210> SEQ ID NO 9
<211> LENGTH: 259
<212> TYPE: PRT
<213> ORGANISM: Arabidopsis

<400> SEQUENCE: 9

```
Val Phe Leu His Leu Leu Ile Ser Gly Ser Gly Ser Thr Pro Pro Leu
  1               5                  10                  15

Thr His Ser Asn Gln Gln Val Ala Ala Thr Arg Trp Leu Pro Ala Thr
             20                  25                  30

Ala Thr Trp Tyr Gly Ser Ala Glu Gly Asp Gly Ser Ser Gly Gly Ala
         35                  40                  45

Cys Gly Tyr Gly Ser Leu Val Asp Val Lys Pro Phe Lys Ala Arg Val
     50                  55                  60

Gly Ala Val Ser Pro Ile Leu Phe Lys Gly Gly Glu Gly Cys Gly Ala
 65                  70                  75                  80

Cys Tyr Lys Val Arg Cys Leu Asp Lys Thr Ile Cys Ser Lys Arg Ala
                 85                  90                  95

Val Thr Ile Ile Ala Thr Asp Gln Ser Pro Ser Gly Pro Ser Ala Lys
            100                 105                 110

Ala Lys His Thr His Phe Asp Leu Ser Gly Ala Ala Phe Gly His Met
        115                 120                 125

Ala Ile Pro Gly His Asn Gly Val Ile Arg Asn Arg Gly Leu Leu Asn
    130                 135                 140

Ile Leu Tyr Arg Arg Thr Ala Cys Lys Tyr Arg Gly Lys Asn Ile Ala
145                 150                 155                 160

Phe His Val Asn Ala Gly Ser Thr Asp Tyr Trp Leu Ser Leu Leu Ile
                165                 170                 175

Glu Tyr Glu Asp Gly Glu Gly Asp Ile Gly Ser Met His Ile Arg Gln
            180                 185                 190

Ala Gly Ser Lys Glu Trp Ile Ser Met Lys His Ile Trp Gly Ala Asn
        195                 200                 205

Trp Cys Ile Val Glu Gly Pro Leu Lys Gly Pro Phe Ser Val Lys Leu
    210                 215                 220

Thr Thr Leu Ser Asn Asn Lys Thr Leu Ser Ala Thr Asp Val Ile Pro
225                 230                 235                 240

Ser Asn Trp Val Pro Lys Ala Tyr Thr Ser Arg Leu Asn Phe Ser
                245                 250                 255

Pro Val Leu
```

<210> SEQ ID NO 10
<211> LENGTH: 261
<212> TYPE: PRT
<213> ORGANISM: Oryza sativa
<220> FEATURE:
<221> NAME/KEY: UNSURE
<222> LOCATION: (226)

<400> SEQUENCE: 10

```
Met Ala Gly Ala Ser Ala Lys Val Val Ala Met Leu Leu Ser Val Leu
  1               5                  10                  15

Ala Thr Tyr Gly Phe Ala Ala Gly Val Val Tyr Thr Asn Asp Trp Leu
             20                  25                  30

Pro Ala Lys Ala Thr Trp Tyr Gly Gln Pro Asn Gly Ala Gly Pro Asp
         35                  40                  45
```

```
Asp Asn Gly Gly Ala Cys Gly Phe Lys Asn Thr Asn Gln Tyr Pro Phe
         50                  55                  60

Met Ser Met Thr Ser Cys Gly Asn Glu Pro Leu Phe Gln Asp Gly Lys
 65                  70                  75                  80

Gly Cys Gly Ala Cys Tyr Gln Ile Arg Cys Thr Asn Asn Pro Ser Cys
                 85                  90                  95

Ser Gly Gln Pro Arg Thr Val Ile Ile Thr Asp Met Asn Tyr Tyr Pro
                100                 105                 110

Val Ala Arg Tyr His Phe Asp Leu Ser Gly Thr Ala Phe Gly Ala Met
            115                 120                 125

Ala Arg Pro Gly Leu Asn Asp Gln Leu Arg His Ala Gly Ile Ile Asp
        130                 135                 140

Ile Gln Phe Arg Arg Val Pro Cys Tyr His Arg Gly Leu Tyr Val Asn
145                 150                 155                 160

Phe His Val Glu Ala Gly Ser Asn Pro Val Tyr Leu Ala Val Leu Val
                165                 170                 175

Glu Phe Ala Asn Lys Asp Gly Thr Val Val Gln Leu Asp Val Met Glu
            180                 185                 190

Ser Leu Pro Ser Gly Lys Pro Thr Arg Val Trp Thr Pro Met Arg Arg
        195                 200                 205

Ser Trp Gly Ser Ile Trp Arg Leu Asp Ala Asn His Arg Leu Gln Gly
210                 215                 220

Pro Xaa Ser Leu Arg Met Val Ser Glu Ser Gly Gln Thr Val Ile Ala
225                 230                 235                 240

His Gln Val Ile Pro Ala Asn Trp Arg Ala Asn Thr Asn Tyr Gly Ser
                245                 250                 255

Lys Val Gln Phe Arg
            260

<210> SEQ ID NO 11
<211> LENGTH: 295
<212> TYPE: PRT
<213> ORGANISM: Oryza sativa
<220> FEATURE:
<221> NAME/KEY: UNSURE
<222> LOCATION: (109)..(142)

<400> SEQUENCE: 11

Thr Arg Leu Tyr Asp His Ile Gly Glu Trp Val Arg Ala Pro Leu Glu
  1               5                  10                  15

Val Asp Pro Arg Val Arg Gly Asp Val Glu Val Val Tyr Tyr Leu
             20                  25                  30

Leu Leu Val Leu Val Val Val Gln Gly Cys Lys Gly Ser Ser Ala Val
             35                  40                  45

Gln Gly Glu Gly Arg Trp Tyr Asn Glu Ser Glu Ala Ile Gly Gly Ala
         50                  55                  60

Ala Ala Trp Gly Asn Ala Lys Ala Thr Trp Tyr Gly Gln Pro Asn Gly
 65                  70                  75                  80

Ala Gly Ala Ala Asp Asn Gly Ala Cys Gly Phe Lys Lys Val Asn
                 85                  90                  95

Gln Tyr Pro Phe Met Gly Met Thr Ser Cys Gly Asn Xaa Pro Leu Tyr
            100                 105                 110

Lys Gly Gly Lys Gly Cys Gly Ser Cys Tyr Arg Val Arg Cys Asn Arg
        115                 120                 125

Asn Pro Ala Cys Ser Gly Asn Ala Gln Thr Val Ala Ile Xaa Asp Met
```

```
                    130                 135                 140
Asn Tyr Phe Pro Leu Ser Gln Tyr His Phe Asp Leu Ser Gly Ile Ala
145                 150                 155                 160

Phe Gly Arg Leu Ala Lys Pro Gly Arg Ala Asp Asp Leu Arg Arg Ala
                    165                 170                 175

Gly Ile Ile Asp Val Gln Phe Ala Arg Val Pro Cys Glu Phe Pro Gly
                180                 185                 190

Leu Lys Val Gly Phe His Val Glu Glu Gly Ser Ser Pro Val Tyr Leu
                195                 200                 205

Ala Val Leu Val Glu Tyr Glu Asn Gly Asp Gly Asp Val Ala Gln Val
                210                 215                 220

Asp Leu Lys Glu Ala Gly Ala Gly Gly Arg Trp Thr Pro Met Arg
225                 230                 235                 240

Glu Ser Trp Gly Ser Val Trp Arg Leu Asp Ser Asn His Arg Leu Arg
                    245                 250                 255

Ala Pro Phe Ser Ile Arg Ile Arg Ser Asp Ser Gly Lys Thr Leu Val
                260                 265                 270

Ala Pro Asp Val Ile Pro Leu Asn Trp Thr Pro Asn Thr Phe Tyr Arg
                275                 280                 285

Ser Phe Val Gln Tyr Ser Ser
                290                 295

<210> SEQ ID NO 12
<211> LENGTH: 260
<212> TYPE: PRT
<213> ORGANISM: Oryza sativa

<400> SEQUENCE: 12

Met Ala Gly Ala Ser Ala Lys Val Val Ala Met Leu Leu Ser Val Leu
1               5                   10                  15

Ala Thr Tyr Gly Phe Ala Ala Gly Val Val Tyr Thr Asn Asp Trp Leu
                20                  25                  30

Pro Ala Lys Ala Thr Trp Tyr Gly Gln Pro Asn Gly Ala Gly Pro Asp
                35                  40                  45

Asp Asn Gly Gly Ala Cys Gly Phe Lys Asn Thr Asn Gln Tyr Pro Phe
            50                  55                  60

Met Ser Met Thr Ser Cys Gly Asn Glu Pro Leu Phe Gln Asp Gly Lys
65              70                  75                  80

Gly Cys Gly Ala Cys Tyr Gln Ile Arg Cys Thr Asn Asn Pro Ser Cys
                    85                  90                  95

Ser Gly Gln Pro Arg Thr Val Ile Ile Thr Asp Met Asn Tyr Tyr Pro
                100                 105                 110

Val Ala Arg Tyr His Phe Asp Leu Ser Gly Thr Ala Phe Gly Ala Met
                115                 120                 125

Ala Arg Pro Gly Leu Asn Asp Gln Leu Arg His Ala Gly Ile Ile Asp
            130                 135                 140

Ile Gln Phe Arg Arg Val Pro Cys Tyr His Arg Gly Leu Tyr Val Asn
145                 150                 155                 160

Phe His Val Glu Ala Gly Ser Asn Pro Val Tyr Leu Ala Val Leu Val
                    165                 170                 175

Glu Phe Ala Asn Lys Asp Gly Thr Val Val Gln Leu Asp Val Met Glu
                180                 185                 190

Ser Leu Pro Ser Gly Lys Pro Thr Arg Val Trp Thr Pro Met Arg Arg
                195                 200                 205
```

```
Ser Trp Gly Ser Ile Trp Arg Leu Asp Ala Asn His Arg Leu Gln Gly
    210                 215                 220

Pro Ser Leu Arg Met Val Ser Glu Ser Gly Gln Thr Val Ile Ala His
225                 230                 235                 240

Gln Val Ile Pro Ala Asn Trp Arg Ala Asn Thr Asn Tyr Gly Ser Lys
                245                 250                 255

Val Gln Phe Arg
            260

<210> SEQ ID NO 13
<211> LENGTH: 283
<212> TYPE: PRT
<213> ORGANISM: Oryza sativa
<220> FEATURE:
<221> NAME/KEY: UNSURE
<222> LOCATION: (134)..(260)

<400> SEQUENCE: 13

Met Gly Ser Leu Ser Ser Leu Ala Ala Ala Val Phe Leu Ser Leu
  1               5                  10                  15

Leu Ala Val Gly His Cys Ala Ala Asp Phe Asn Ala Thr Asp Ala
                 20                  25                  30

Asp Ala Asp Phe Ala Gly Asn Gly Val Asp Phe Asn Ser Ser Asp Ala
                35                  40                  45

Ala Val Tyr Trp Gly Pro Trp Thr Lys Ala Arg Ala Thr Trp Tyr Gly
    50                  55                  60

Gln Pro Asn Gly Ala Gly Pro Asp Asp Asn Gly Ala Cys Gly Phe
 65                 70                  75                  80

Lys His Thr Asn Gln Tyr Pro Phe Met Ser Met Thr Ser Cys Gly Asn
                85                  90                  95

Gln Pro Leu Phe Lys Asp Gly Lys Gly Cys Gly Ser Cys Tyr Lys Ile
                100                 105                 110

Arg Cys Thr Lys Asp Gln Ser Cys Ser Gly Arg Ser Thr Val Ile Ile
            115                 120                 125

Thr Asp Met Asn Tyr Xaa Pro Val Ala Pro Phe His Phe Asp Leu Ser
    130                 135                 140

Gly Thr Ala Phe Gly Arg Leu Ala Xaa Xaa Gly Leu Asn Asp Lys Leu
145                 150                 155                 160

Arg His Ser Gly Ile Ile Asp Ile Phe Thr Val Pro Cys Glu Phe Pro
                165                 170                 175

Gly Leu Lys Ile Gly Phe His Val Glu Glu Tyr Ser Asn Pro Val Tyr
                180                 185                 190

Phe Ala Val Leu Val Glu Tyr Xaa Asp Gly Asp Gly Asp Val Val Gln
            195                 200                 205

Val Asp Leu Met Glu Ser Lys Arg Arg Thr Gly Arg Arg Gly Arg
    210                 215                 220

Trp Thr Pro Met Arg Glu Ser Trp Gly Ser Ile Trp Arg Leu Asp Thr
225                 230                 235                 240

Asn His Arg Leu Gln Ala Pro Phe Ser Ile Arg Ile Arg Asn Glu Ser
                245                 250                 255

Gly Lys Thr Xaa Val Ala Asn Asn Val Ile Pro Ala Asn Trp Arg Pro
            260                 265                 270

Asn Thr Phe Tyr Arg Ser Phe Val Gln Tyr Ser
                275                 280

<210> SEQ ID NO 14
```

```
<211> LENGTH: 126
<212> TYPE: PRT
<213> ORGANISM: Oryza sativa
<220> FEATURE:
<221> NAME/KEY: UNSURE
<222> LOCATION: (104)..(122)

<400> SEQUENCE: 14
```

Met Val Ser Arg Gly Thr Phe Val Phe Ala Val Leu Val Ala Leu Pro
 1               5                  10                  15

Ile Leu Ser Leu Pro Val Ser Gly Tyr Glu Gln Asn Tyr Thr Ala Gly
                20                  25                  30

Arg Arg Ser Thr Met Ser Leu Gly Arg Gly Tyr Gly Trp Ser Ser Gly
            35                  40                  45

Gly Ala Thr Trp Tyr Gly Gly Pro Gln Gly Asp Gly Ser Glu Gly Gly
        50                  55                  60

Ala Cys Gly Tyr Gln Ser Ala Val Gly Gln Arg Arg Phe Ser Ser Met
65                  70                  75                  80

Ile Ala Ala Gly Gly Pro Ser Leu Phe Lys Asn Gly Lys Gly Cys Gly
                85                  90                  95

Ser Cys Tyr Gln Ile Lys Cys Xaa Gly Asn Arg Ala Phe Phe Gly Arg
                100                 105                 110

Gln Xaa Pro Ser Xaa Ser Thr Ser Xaa Leu Glu Gly Tyr
            115                 120                 125

```
<210> SEQ ID NO 15
<211> LENGTH: 90
<212> TYPE: PRT
<213> ORGANISM: Oryza sativa
<220> FEATURE:
<221> NAME/KEY: UNSURE
<222> LOCATION: (63)

<400> SEQUENCE: 15
```

Met Ala Ala Arg Met Gly Ser Lys Val Ala Ala Ile Leu Ala Ile Leu
 1               5                  10                  15

Ser Val Leu Val Val His Gly Ser Cys Lys Gly His Pro Val Asn Tyr
                20                  25                  30

Asn Val Ser Asp Ala Ser Ala Tyr Gly Ser Gly Trp Leu Pro Ala Arg
            35                  40                  45

Ala Thr Trp Tyr Gly Ala Pro Thr Gly Ala Gly Pro Asp Gly Xaa Asn
        50                  55                  60

Gly Gly Ala Cys Gly Val Gln Glu Arg Glu Pro Val Pro Ile Leu Val
65                  70                  75                  80

His Asp Leu Leu Arg Lys Arg Ala His Phe
                85                  90

```
<210> SEQ ID NO 16
<211> LENGTH: 277
<212> TYPE: PRT
<213> ORGANISM: Glycine max

<400> SEQUENCE: 16
```

Met Ala Leu Thr Leu Gln Arg Ala Leu Ser Glu Leu Leu Thr Leu Ile
 1               5                  10                  15

Ala Ile Leu Ser Ile Phe Leu Val Ile Pro Ser Phe Cys Phe Asn Pro
                20                  25                  30

Lys Lys Leu Tyr Asn Ala Ser Tyr Tyr Ser Pro Ser Ser Asp Trp
            35                  40                  45

```
Ser Pro Ala Val Ala Thr Trp Tyr Gly Pro Ala Asn Gly Asp Gly Ser
    50                  55                  60

Glu Gly Gly Ala Cys Gly Tyr Gly Asn Ala Val Gly Gln Pro Pro Phe
 65                  70                  75                  80

Ser Ser Leu Ile Ser Ala Gly Ser Pro Leu Ile Tyr Asp Ser Gly Gly
                 85                  90                  95

Lys Gly Cys Gly Ser Cys Glu Val Lys Cys Thr Gly Asn Ser Ala Cys
            100                 105                 110

Ser Gly Asn Pro Val Lys Val Val Ile Thr Asp Glu Cys Ala Gly Cys
            115                 120                 125

Gly Ser Asp Ala Gln Tyr His Phe Asp Leu Ser Gly Asn Ala Phe Gly
    130                 135                 140

Ala Met Ala Ile Ile Gly Gln Asp Glu Asn Leu Arg Asn Ala Gly Lys
145                 150                 155                 160

Ile Asn Ile Gln His Arg Arg Ile Glu Cys Asn Tyr Pro Gly Arg Ser
                165                 170                 175

Ile Ala Phe His Val Asp Ser Gly Ser Asn Gln Glu Tyr Phe Ala Thr
            180                 185                 190

Leu Val Glu Tyr Glu Asp Gly Asp Gly Asp Leu Leu Ala Lys Glu Leu
        195                 200                 205

Lys Glu Ala Leu Asp Ser Gly Ser Trp Asp Ser Met Gln Gln Ser Trp
    210                 215                 220

Gly Ala Val Trp Lys Phe Asp Lys Gly Ser Pro Leu Arg Ala Pro Phe
225                 230                 235                 240

Ser Ile Lys Leu Thr Thr Leu Glu Ser Gly Gln Thr Ile Val Ala Asn
                245                 250                 255

Asn Asn Val Ile Pro Ala Trp Thr Pro Gly Gln Thr Tyr Arg Ser Ile
            260                 265                 270

Val Asn Phe Ala Thr
            275

<210> SEQ ID NO 17
<211> LENGTH: 273
<212> TYPE: PRT
<213> ORGANISM: Artificial Sequence
<220> FEATURE:
<223> OTHER INFORMATION: Description of Artificial Sequence: beta2
      predicted protein

<400> SEQUENCE: 17

Met Thr Ile Leu Val Val Asp Arg Tyr Tyr Met Leu Met Asn Leu Leu
  1               5                  10                  15

Phe Ala Leu Thr Cys Leu Leu Leu Asn Leu Thr His Cys Phe Ser Pro
             20                  25                  30

Lys Lys Phe Asn Ile Ser Ala Ala Thr Thr Ser Asp Ser Asp Trp Ser
         35                  40                  45

Ile Ala Gly Ser Thr Trp Tyr Gly Asn Pro Thr Gly Tyr Gly Ser Asp
    50                  55                  60

Gly Gly Ala Cys Gly Tyr Gly Asn Ala Val Ala Gln Pro Pro Phe Ser
 65                  70                  75                  80

Lys Met Val Ser Ala Gly Gly Pro Ser Leu Phe Lys Ser Gly Lys Gly
                 85                  90                  95

Cys Gly Ala Cys Tyr Gln Val Lys Cys Thr Ser Lys Ser Ala Cys Ser
            100                 105                 110

Lys Asn Pro Val Thr Val Val Ile Thr Asp Glu Cys Pro Gly Cys Val
            115                 120                 125
```

```
Lys Glu Ser Val His Phe Asp Leu Ser Gly Thr Ala Phe Gly Ala Met
130                 135                 140

Ala Ile Ser Gly Gln Asp Ser Gln Leu Arg Asn Val Gly Glu Leu Gln
145                 150                 155                 160

Ile Leu Tyr Lys Lys Val Glu Cys Asn Tyr Ile Gly Lys Thr Val Thr
                165                 170                 175

Phe Gln Val Asp Lys Gly Ser Asn Ala Asn Ser Phe Ala Val Leu Val
                180                 185                 190

Ala Tyr Val Asn Gly Asp Gly Glu Ile Gly Arg Ile Glu Leu Lys Gln
                195                 200                 205

Ala Leu Asp Ser Asp Lys Trp Leu Ser Met Ser Gln Ser Trp Gly Ala
                210                 215                 220

Val Trp Lys Leu Asp Val Ser Ser Pro Leu Arg Ala Pro Leu Ser Leu
225                 230                 235                 240

Arg Val Thr Ser Leu Glu Ser Gly Lys Thr Val Val Ala Ser Asn Val
                245                 250                 255

Ile Pro Ala Asn Trp Gln Pro Gly Ala Ile Tyr Lys Ser Asn Val Asn
                260                 265                 270

Phe

<210> SEQ ID NO 18
<211> LENGTH: 269
<212> TYPE: PRT
<213> ORGANISM: Zea mays

<400> SEQUENCE: 18

Met Gly Ser Leu Ala Asn Asn Ile Met Val Val Gly Ala Val Leu Ala
1               5                   10                  15

Ala Leu Val Val Gly Gly Ser Cys Gly Pro Pro Lys Val Pro Pro Gly
                20                  25                  30

Pro Asn Ile Thr Thr Asn Tyr Asn Gly Lys Trp Leu Thr Ala Arg Ala
                35                  40                  45

Thr Trp Tyr Gly Gln Pro Asn Gly Ala Gly Ala Pro Asp Asn Gly Gly
    50                  55                  60

Ala Cys Gly Ile Lys Asn Val Asn Leu Pro Pro Tyr Ser Gly Met Thr
65                  70                  75                  80

Ala Cys Gly Asn Val Pro Ile Phe Lys Asp Gly Lys Gly Cys Gly Ser
                85                  90                  95

Cys Tyr Glu Val Arg Cys Lys Glu Lys Pro Glu Cys Ser Gly Asn Pro
                100                 105                 110

Val Thr Val Phe Ile Thr Asp Met Met Tyr Glu Pro Ile Ala Pro Tyr
                115                 120                 125

His Phe Asp Leu Ser Gly Lys Ala Phe Gly Ser Leu Ala Lys Pro Gly
130                 135                 140

Leu Asn Asp Lys Leu Arg His Cys Gly Ile Met Asp Val Glu Phe Arg
145                 150                 155                 160

Arg Val Arg Cys Lys Tyr Pro Ala Gly Gln Lys Ile Val Phe His Ile
                165                 170                 175

Glu Lys Gly Cys Asn Pro Asn Tyr Val Ala Val Leu Val Lys Phe Val
                180                 185                 190

Ala Asp Asp Gly Asp Ile Val Leu Met Glu Ile Gln Asp Lys Leu Ser
                195                 200                 205

Ala Glu Trp Lys Pro Met Lys Leu Ser Trp Gly Ala Ile Trp Arg Met
210                 215                 220
```

```
Asp Thr Ala Lys Ala Leu Lys Gly Pro Phe Ser Ile Arg Leu Thr Ser
225                 230                 235                 240

Glu Ser Gly Lys Lys Val Ile Ala Lys Asp Ile Ile Pro Ala Asn Trp
            245                 250                 255

Arg Pro Asp Ala Val Tyr Thr Ser Asn Val Gln Phe Tyr
        260                 265
```

<210> SEQ ID NO 19
<211> LENGTH: 263
<212> TYPE: PRT
<213> ORGANISM: Lolium perenne

<400> SEQUENCE: 19

```
Met Ala Ser Ser Ser Val Leu Leu Val Ala Leu Phe Ala Val
 1               5                  10                  15

Phe Leu Gly Ser Ala His Gly Ile Ala Lys Val Pro Gly Pro Asn
                20                  25                  30

Ile Thr Ala Glu Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
    50                  55                  60

Gly Tyr Lys Asn Val Asp Lys Ala Pro Phe Asn Gly Met Thr Gly Cys
 65                 70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
        115                 120                 125

Asp Leu Ser Gly His Ala Phe Gly Ser Met Ala Lys Lys Gly Glu Glu
    130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
            260
```

<210> SEQ ID NO 20
<211> LENGTH: 247
<212> TYPE: PRT
<213> ORGANISM: Glycine max

<400> SEQUENCE: 20

```
Met Ala Leu Thr Leu Gln Arg Ala Leu Ser Glu Leu Leu Thr Leu Ile
 1               5                  10                  15
```

```
Ala Ile Leu Ser Ile Phe Leu Val Ile Pro Ser Phe Cys Phe Asn Pro
            20                  25                  30

Lys Lys Leu Tyr Asn Ala Ser Tyr Tyr Ser Pro Ser Ser Ser Asp Trp
        35                  40                  45

Ser Pro Ala Val Ala Thr Trp Tyr Gly Pro Ala Asn Gly Asp Gly Ser
    50                  55                  60

Glu Gly Gly Ala Cys Gly Tyr Gly Asn Ala Val Gly Gln Pro Pro Phe
65                  70                  75                  80

Ser Ser Leu Ile Ser Ala Gly Ser Pro Leu Ile Tyr Asp Ser Gly Lys
                85                  90                  95

Gly Cys Gly Ser Cys Tyr Glu Val Lys Cys Thr Gly Asn Ser Ala Cys
                100                 105                 110

Ser Gly Asn Pro Val Lys Val Val Ile Thr Asp Glu Cys Ala Gly Cys
            115                 120                 125

Gly Ser Asp Ala Gln Tyr His Phe Asp Leu Ser Gly Asn Ala Phe Gly
        130                 135                 140

Ala Met Ala Ile Ser Gly Gln Asp Glu Asn Leu Arg Asn Ala Gly Lys
145                 150                 155                 160

Ile Asn Ile Gln His Arg Arg Ile Glu Cys Asn Tyr Pro Gly Arg Ser
                165                 170                 175

Ile Ala Phe His Val Asp Ser Gly Ser Asn Gln Glu Tyr Phe Ala Thr
                180                 185                 190

Leu Val Glu Tyr Glu Asp Gly Asp Gly Asp Leu Ala Lys Val Glu Leu
            195                 200                 205

Lys Glu Ala Leu Asp Ser Gly Ser Trp Asp Ser Met Gln Gln Ser Trp
        210                 215                 220

Gly Ala Val Trp Lys Phe Asp Lys Gly Ser Pro Leu Arg Ala Pro Phe
225                 230                 235                 240

Ser Ile Lys Leu Thr Thr Leu
                245

<210> SEQ ID NO 21
<211> LENGTH: 258
<212> TYPE: PRT
<213> ORGANISM: Arabidopsis

<400> SEQUENCE: 21

Val Phe Leu His Leu Leu Ile Ser Gly Ser Gly Ser Thr Pro Pro Leu
1               5                   10                  15

Thr His Ser Asn Gln Gln Val Ala Ala Thr Arg Trp Leu Pro Ala Thr
            20                  25                  30

Ala Thr Trp Tyr Gly Ser Ala Glu Gly Asp Gly Ser Ser Gly Gly Ala
        35                  40                  45

Cys Gly Tyr Gly Ser Leu Val Asp Val Lys Pro Phe Lys Ala Arg Val
    50                  55                  60

Gly Ala Val Ser Pro Ile Leu Phe Lys Gly Glu Gly Cys Gly Ala
65                  70                  75                  80

Cys Tyr Lys Val Arg Cys Leu Asp Lys Thr Ile Cys Ser Lys Arg Ala
                85                  90                  95

Val Thr Ile Ile Ala Thr Asp Gln Ser Pro Ser Gly Pro Ser Ala Lys
            100                 105                 110

Ala Lys His Thr His Phe Asp Leu Ser Gly Ala Ala Phe Gly His Met
        115                 120                 125

Ala Ile Pro Gly His Asn Gly Val Ile Arg Asn Arg Gly Leu Leu Asn
```

```
            130                 135                 140
Ile Leu Tyr Arg Arg Thr Ala Cys Lys Tyr Arg Gly Lys Asn Ile Ala
145                 150                 155                 160

Phe His Val Asn Ala Gly Ser Thr Asp Tyr Trp Leu Ser Leu Leu Ile
                165                 170                 175

Glu Tyr Glu Asp Gly Glu Gly Asp Ile Gly Ser Met His Ile Arg Gln
            180                 185                 190

Ala Gly Ser Lys Glu Trp Ile Ser Met Lys His Ile Trp Gly Ala Asn
            195                 200                 205

Trp Cys Ile Val Glu Gly Pro Leu Lys Gly Pro Phe Ser Val Lys Leu
        210                 215                 220

Thr Thr Leu Ser Asn Asn Lys Thr Leu Ser Ala Thr Asp Val Ile Pro
225                 230                 235                 240

Ser Asn Trp Val Pro Lys Ala Thr Tyr Thr Ser Arg Leu Asn Phe Ser
                245                 250                 255

Pro Val

<210> SEQ ID NO 22
<211> LENGTH: 250
<212> TYPE: PRT
<213> ORGANISM: Cucumis sativus

<400> SEQUENCE: 22

Met Ala Phe Ser Tyr Ser Pro Phe Ser Ser Leu Phe Leu Pro Phe
1               5                   10                  15

Phe Phe Val Phe Thr Phe Ala Asp Tyr Gly Gly Trp Gln Ser Gly His
                20                  25                  30

Ala Thr Phe Tyr Gly Gly Gly Asp Ala Ser Gly Thr Met Gly Gly Ala
            35                  40                  45

Cys Gly Tyr Gly Asn Leu Tyr Ser Gln Gly Thr Gly Thr Asn Thr Val
        50                  55                  60

Ala Leu Ser Thr Ala Leu Phe Asn Asn Gly Leu Ser Cys Gly Ala Cys
65                  70                  75                  80

Phe Glu Met Thr Cys Thr Asn Asp Pro Lys Trp Cys Leu Pro Gly Thr
                85                  90                  95

Ile Arg Val Thr Ala Thr Asn Phe Cys Pro Pro Asn Phe Ala Leu Pro
                100                 105                 110

Asn Asn Asn Gly Gly Trp Cys Asn Pro Pro Leu Gln His Phe Asp Met
            115                 120                 125

Ala Glu Pro Ala Phe Leu Gln Ile Ala Gln Tyr Arg Ala Gly Ile Val
            130                 135                 140

Pro Val Ser Phe Arg Arg Val Pro Cys Met Lys Lys Gly Gly Val Arg
145                 150                 155                 160

Phe Thr Ile Asn Gly His Ser Tyr Phe Asn Leu Val Leu Ile Thr Asn
                165                 170                 175

Val Gly Gly Ala Gly Asp Val His Ser Val Ser Ile Lys Gly Ser Arg
            180                 185                 190

Thr Gly Trp Gln Ser Met Ser Arg Asn Trp Gly Gln Asn Trp Gln Ser
            195                 200                 205

Asn Asn Tyr Leu Asn Gly Gln Gly Leu Ser Phe Gln Val Thr Leu Ser
        210                 215                 220

Asp Gly Arg Thr Leu Thr Ala Tyr Asn Leu Val Pro Ser Asn Trp Gln
225                 230                 235                 240

Phe Gly Gln Thr Tyr Glu Gly Pro Gln Phe
```

-continued

<210> SEQ ID NO 23
<211> LENGTH: 258
<212> TYPE: PRT
<213> ORGANISM: Cucumis sativus

<400> SEQUENCE: 23

```
Met Glu Lys Leu Pro Phe Ala Phe Ala Phe Leu Ala Leu Ser Asn
 1               5                  10                  15

Phe Phe Phe Leu Phe Val Asn Ala Phe Thr Ala Ser Gly Trp Ala Pro
            20                  25                  30

Ala His Ala Thr Phe Tyr Gly Glu Ser Asp Ala Ser Gly Thr Met Gly
        35                  40                  45

Gly Ala Cys Gly Tyr Gly Asn Leu Tyr Gln Thr Gly Tyr Gly Thr Arg
    50                  55                  60

Thr Ala Ala Leu Ser Thr Ala Leu Phe Asn Asp Gly Ala Ser Cys Gly
65                  70                  75                  80

Gln Cys Phe Lys Ile Ile Cys Asp Tyr Lys Thr Asp Pro Arg Trp Cys
                85                  90                  95

Ile Lys Gly Ala Ser Val Thr Ile Thr Ala Thr Asn Phe Cys Pro Pro
            100                 105                 110

Asn Tyr Ala Leu Pro Asn Asn Asn Gly Gly Trp Cys Asn Pro Pro Leu
        115                 120                 125

Lys His Phe Asp Met Ala Gln Pro Ala Trp Gln Lys Ile Gly Ile Tyr
    130                 135                 140

Arg Gly Gly Ile Ile Pro Val Leu Tyr Gln Arg Val Pro Cys Lys Lys
145                 150                 155                 160

Arg Gly Gly Val Arg Phe Thr Val Asn Gly Arg Asp Tyr Phe Glu Leu
                165                 170                 175

Val Leu Ile Thr Asn Val Gly Ala Gly Asp Ile Lys Ser Val Ser
            180                 185                 190

Ile Lys Gly Ser Lys Ser Ser Asn Trp Thr Pro Met Ser Arg Asn Trp
        195                 200                 205

Gly Ala Asn Trp Gln Ser Asn Ser Tyr Leu Asn Gly Gln Ser Leu Ser
    210                 215                 220

Phe Lys Val Thr Thr Ser Asp Gly Gln Val Gln Val Phe Asn Asn Val
225                 230                 235                 240

Val Pro Ser Ser Trp Arg Phe Gly Gln Thr Phe Ala Ser Lys Val Gln
                245                 250                 255

Phe Ser
```

<210> SEQ ID NO 24
<211> LENGTH: 15
<212> TYPE: PRT
<213> ORGANISM: Cucumis sativus

<400> SEQUENCE: 24

```
Ala Ser Gly Thr Met Gly Gly Ala Cys Gly Tyr Gly Asn Leu Tyr
 1               5                  10                  15
```

<210> SEQ ID NO 25
<211> LENGTH: 15
<212> TYPE: PRT
<213> ORGANISM: Lolium perenne

<400> SEQUENCE: 25

```
Gly Pro Lys Asp Asn Gly Gly Ala Cys Gly Tyr Lys Asn Val Asp
 1               5                  10                 15
```

<210> SEQ ID NO 26
<211> LENGTH: 15
<212> TYPE: PRT
<213> ORGANISM: Cucumis sativus

<400> SEQUENCE: 26

```
Asn Gly Leu Ser Cys Gly Ala Cys Phe Glu Met Thr Cys Thr Asn
 1               5                  10                 15
```

<210> SEQ ID NO 27
<211> LENGTH: 15
<212> TYPE: PRT
<213> ORGANISM: Lolium perenne

<400> SEQUENCE: 27

```
Asp Gly Arg Gly Cys Gly Ser Cys Phe Glu Ile Lys Cys Thr Lys
 1               5                  10                 15
```

<210> SEQ ID NO 28
<211> LENGTH: 15
<212> TYPE: PRT
<213> ORGANISM: Cucumis sativus

<400> SEQUENCE: 28

```
Gln His Phe Asp Met Ala Glu Pro Ala Phe Leu Gln Ile Ala Gln
 1               5                  10                 15
```

<210> SEQ ID NO 29
<211> LENGTH: 15
<212> TYPE: PRT
<213> ORGANISM: Lolium perenne

<400> SEQUENCE: 29

```
Tyr His Phe Asp Leu Ser Gly Met Ala Phe Gly Ser Met Ala Lys
 1               5                  10                 15
```

<210> SEQ ID NO 30
<211> LENGTH: 15
<212> TYPE: PRT
<213> ORGANISM: Cucumis sativus

<400> SEQUENCE: 30

```
Ala Gly Ile Val Pro Val Ser Phe Arg Arg Val Pro Cys Met Lys
 1               5                  10                 15
```

<210> SEQ ID NO 31
<211> LENGTH: 15
<212> TYPE: PRT
<213> ORGANISM: Lolium perenne

<400> SEQUENCE: 31

```
Ala Gly Glu Leu Glu Leu Gln Phe Arg Arg Val Lys Cys Lys Tyr
 1               5                  10                 15
```

<210> SEQ ID NO 32
<211> LENGTH: 15
<212> TYPE: PRT
<213> ORGANISM: Cucumis sativus

<400> SEQUENCE: 32

```
Asn Val Gly Gly Ala Gly Asp Val His Ser Val Ser Ile Lys Gly
 1               5                  10                 15
```

```
<210> SEQ ID NO 33
<211> LENGTH: 15
<212> TYPE: PRT
<213> ORGANISM: Lolium perenne

<400> SEQUENCE: 33

Tyr Val Asp Gly Asp Gly Asp Val Val Ala Val Asp Ile Lys Glu
 1               5                  10                  15

<210> SEQ ID NO 34
<211> LENGTH: 5
<212> TYPE: PRT
<213> ORGANISM: beta-expansin

<400> SEQUENCE: 34

Gly Gly Ala Cys Gly
 1               5

<210> SEQ ID NO 35
<211> LENGTH: 6
<212> TYPE: PRT
<213> ORGANISM: beta-expansin

<400> SEQUENCE: 35

His Phe Asp Leu Ser Gly
 1               5

<210> SEQ ID NO 36
<211> LENGTH: 261
<212> TYPE: PRT
<213> ORGANISM: Oryza sativa

<400> SEQUENCE: 36

Met Ala Gly Ser Ser Ala Ala Thr Ser Cys Ala Arg Phe Leu Ala Leu
 1               5                  10                  15

Leu Ala Thr Cys Leu Leu Trp Asn Glu Ala Ala Ser Phe Thr Ala Ser
                20                  25                  30

Gly Trp Asn Lys Ala Phe Ala Thr Phe Tyr Gly Gly Ser Asp Ala Ser
            35                  40                  45

Gly Thr Met Gly Gly Ala Cys Gly Tyr Gly Asp Leu Tyr Ser Thr Gly
        50                  55                  60

Tyr Gly Thr Asn Thr Ala Ala Leu Ser Thr Val Leu Phe Asn Asp Gly
 65                  70                  75                  80

Ala Ser Cys Gly Gln Cys Tyr Arg Ile Met Cys Asp Tyr Gln Ala Asp
                85                  90                  95

Arg Arg Phe Cys Ile Ser Gly Thr Ser Val Thr Ile Thr Ala Thr Asn
            100                 105                 110

Leu Cys Pro Pro Asn Tyr Ala Leu Pro Asn Asp Ala Gly Gly Trp Cys
        115                 120                 125

Asn Pro Pro Arg Gln His Phe Asp Met Ala Glu Pro Ala Trp Leu Lys
    130                 135                 140

Ile Gly Val Tyr Val Gly Gly Ile Val Pro Val Met Tyr Gln Arg Val
145                 150                 155                 160

Pro Cys Ala Lys Gln Gly Gly Val Arg Phe Thr Ile Asn Gly Arg Asp
                165                 170                 175

Tyr Phe Glu Leu Val Leu Val Ser Asn Val Gly Gly Val Gly Ser Ile
            180                 185                 190

Gln Ser Val Ser Ile Lys Gly Ser Arg Thr Gly Trp Met Ala Met Ser
```

-continued

```
            195                 200                 205
Arg Asn Trp Gly Val Asn Trp Gln Ser Asn Ala Tyr Leu Asp Gly Gln
        210                 215                 220

Ser Leu Ser Phe Lys Val Thr Ser Ser Asp Gly Gln Thr Leu Thr Phe
225                 230                 235                 240

Leu Asp Val Ala Pro Ala Gly Trp Thr Phe Gly Gln Thr Phe Ser Thr
                245                 250                 255

Ser Gln Gln Phe Ser
            260

<210> SEQ ID NO 37
<211> LENGTH: 254
<212> TYPE: PRT
<213> ORGANISM: Arabidopsis

<400> SEQUENCE: 37

Met Ala Leu Val Thr Phe Leu Ile Ala Thr Leu Gly Ala Met Thr Ser
 1               5                  10                  15

Asn Asn Ser Ala Arg Asp Val Asn Gly Tyr Ala Gly Gly Gly Trp Val
            20                  25                  30

Asn Ala His Ala Thr Phe Tyr Gly Gly Asp Ala Ser Gly Thr Met
        35                  40                  45

Gly Gly Ala Cys Gly Tyr Gly Asn Leu Tyr Ser Gln Gly Tyr Gly Thr
    50                  55                  60

Asn Thr Ala Ala Leu Ser Thr Ala Leu Phe Asn Asn Gly Leu Ser Cys
65                  70                  75                  80

Gly Ala Cys Phe Glu Ile Arg Cys Gln Asn Asp Gly Lys Trp Cys Leu
                85                  90                  95

Pro Gly Ser Ile Val Val Thr Ala Thr Asn Phe Cys Pro Pro Asn Asn
            100                 105                 110

Ala Leu Pro Asn Asn Ala Gly Gly Trp Cys Asn Pro Pro Gln Gln His
        115                 120                 125

Phe Asp Leu Ser Gln Pro Val Phe Gln Arg Ile Ala Gln Tyr Arg Ala
    130                 135                 140

Gly Ile Val Pro Val Ala Tyr Arg Arg Val Pro Cys Val Arg Arg Gly
145                 150                 155                 160

Gly Ile Arg Phe Thr Ile Asn Gly His Ser Tyr Phe Asn Leu Val Leu
                165                 170                 175

Ile Thr Asn Val Gly Gly Ala Gly Asp Val His Ser Ala Met Val Lys
            180                 185                 190

Gly Ser Arg Thr Gly Trp Gln Ala Met Ser Arg Asn Trp Gly Gln Asn
        195                 200                 205

Trp Gln Ser Asn Ser Tyr Leu Asn Gly Gln Ser Leu Ser Phe Lys Val
    210                 215                 220

Thr Thr Ser Asp Gly Gln Thr Ile Val Ser Asn Asn Val Ala Asn Ala
225                 230                 235                 240

Gly Trp Ser Phe Gly Gln Thr Phe Thr Gly Ala Gln Leu Arg
                245                 250
```